(12) United States Patent
Berndl et al.

(10) Patent No.: US 8,470,347 B2
(45) Date of Patent: *Jun. 25, 2013

(54) SELF-EMULSIFYING ACTIVE SUBSTANCE FORMULATION AND USE OF THIS FORMULATION

(75) Inventors: Gunther Berndl, Herxheim (DE); Jörg Breitenbach, Mannheim (DE); Robert Heger, Heidelberg (DE); Michael Stadler, Neulußheim (DE); Peter Wilke, Ludwigshafen (DE); Jörg Rosenberg, Ellerstadt (DE)

(73) Assignee: AbbVie Deutschland GmbH and Co KG, Wiesbaden (DE)

( * ) Notice: Subject to any disclaimer, the term of this patent is extended or adjusted under 35 U.S.C. 154(b) by 1937 days.

This patent is subject to a terminal disclaimer.

(21) Appl. No.: 10/296,451

(22) PCT Filed: May 29, 2001

(86) PCT No.: PCT/EP01/06116
§ 371 (c)(1),
(2), (4) Date: Nov. 25, 2002

(87) PCT Pub. No.: WO01/91727
PCT Pub. Date: Dec. 6, 2001

(65) Prior Publication Data
US 2004/0013697 A1 Jan. 22, 2004

(30) Foreign Application Priority Data
May 30, 2000 (DE) ................................ 100 26 698

(51) Int. Cl.
*A61K 8/20* (2006.01)
*A61K 8/73* (2006.01)
*A61K 8/81* (2006.01)

(52) U.S. Cl.
USPC .................... 424/401; 424/70.13; 424/70.15; 424/70.16

(58) Field of Classification Search
USPC ................................. 424/497, 422
See application file for complete search history.

(56) References Cited

U.S. PATENT DOCUMENTS

| | | |
|---|---|---|
| 4,540,602 A | 9/1985 | Motoyama et al. |
| 4,590,065 A | 5/1986 | Piechota, Jr. et al. |
| 4,758,427 A | 7/1988 | Leeson |
| 4,769,235 A | 9/1988 | Schlesinger et al. |
| 4,769,236 A | 9/1988 | Panoz et al. |
| 4,801,460 A | 1/1989 | Goertz et al. |
| 4,804,699 A | 2/1989 | Nelson et al. |
| 4,806,337 A | 2/1989 | Snipes et al. |
| 4,851,438 A | 7/1989 | Flashinski |
| 4,880,585 A | 11/1989 | Klimesch et al. |
| 4,904,699 A | 2/1990 | Bauer |
| 4,957,681 A | 9/1990 | Klimesch et al. |
| 4,996,058 A | 2/1991 | Sinnreich |
| 5,009,701 A | 4/1991 | Plath et al. |
| 5,073,379 A | 12/1991 | Klimesch et al. |
| 5,145,683 A | 9/1992 | Rhodes |
| 5,281,420 A | 1/1994 | Kelm et al. |
| 5,290,351 A | 3/1994 | Ritter |
| 5,368,864 A | 11/1994 | Lahr et al. |
| 5,405,616 A | 4/1995 | Wunderlich et al. |
| 5,456,923 A | 10/1995 | Nakamichi et al. |
| 5,476,667 A | 12/1995 | Kristensen et al. |
| 5,490,990 A | 2/1996 | Grabowski et al. |
| 5,501,858 A | 3/1996 | Fuisz |
| 5,525,628 A | 6/1996 | Nicola et al. |
| 5,541,206 A | 7/1996 | Kempf et al. |
| 5,545,628 A | 8/1996 | Deboeck et al. |
| 5,552,159 A | 9/1996 | Mueller et al. |
| 5,559,158 A | 9/1996 | Al-Razzak et al. |
| 5,567,823 A | 10/1996 | Tien et al. |
| 5,610,193 A | 3/1997 | Al-Razzak et al. |
| 5,641,516 A | 6/1997 | Grabowski et al. |
| 5,648,497 A | 7/1997 | Kempf et al. |
| 5,654,003 A | 8/1997 | Fuisz et al. |
| 5,674,882 A | 10/1997 | Kempf et al. |
| 5,684,040 A * | 11/1997 | Grabowski et al. ........... 514/457 |

(Continued)

FOREIGN PATENT DOCUMENTS

| | | |
|---|---|---|
| AU | 31138/93 | 7/1993 |
| CA | 1270201 A1 * | 6/1990 |

(Continued)

OTHER PUBLICATIONS

Abu T. M. "Bioavailability Enhancement of Poorly Water-Soluble Drugs by Solid Dispersion in Surface Active And Self-Emulsifying vehicles", provided by Applicant in IDS dated Jul. 21, 2003 (provided by Applicant).*

(Continued)

*Primary Examiner* — Michael G Hartley
*Assistant Examiner* — Nabila Ebrahim
(74) *Attorney, Agent, or Firm* — Xu Zhang

(57) ABSTRACT

The present invention relates to self-emulsifying formulations based on an active ingredient component and a formulation base with a lipid component and with a binder component and to the use of this formulation as dosage form in the life science sector. The invention also describes a process for producing self-emulsifying formulations by mixing the formulation components to form a plastic mixture and, where appropriate, to manufacture the formulations as dosage form advantageously by use of melt extrusion. The formulations spontaneously form emulsions in water or aqueous media.

29 Claims, No Drawings

U.S. PATENT DOCUMENTS

| | | | |
|---|---|---|---|
| 5,695,784 A | 12/1997 | Pollinger et al. | |
| 5,700,410 A | 12/1997 | Nakamichi et al. | |
| 5,707,648 A | 1/1998 | Yiv | |
| 5,725,878 A | 3/1998 | Al-Razzak et al. | |
| 5,727,878 A | 3/1998 | Sullivan, Jr. | |
| 5,741,519 A | 4/1998 | Rosenberg et al. | |
| 5,756,450 A | 5/1998 | Hahn et al. | |
| 5,762,961 A | 6/1998 | Roser et al. | |
| 5,773,025 A | 6/1998 | Baichwal | |
| 5,776,495 A | 7/1998 | Duclos et al. | |
| 5,834,472 A | 11/1998 | Sangekar et al. | |
| 5,858,401 A | 1/1999 | Bhalani et al. | 424/450 |
| 5,889,051 A | 3/1999 | Chen et al. | |
| 5,897,910 A | 4/1999 | Rosenberg et al. | |
| 5,914,332 A | 6/1999 | Sham et al. | |
| 5,935,936 A | 8/1999 | Fasbender et al. | |
| 5,939,099 A | 8/1999 | Grabowski et al. | |
| 5,945,123 A | 8/1999 | Hermelin | |
| 5,945,127 A | 8/1999 | Breitenbach et al. | |
| 5,948,426 A | 9/1999 | Jefferies | |
| 5,948,436 A | 9/1999 | Al-Razzak et al. | |
| 5,955,475 A | 9/1999 | Krape et al. | |
| 5,958,452 A | 9/1999 | Oshlack et al. | |
| 5,958,455 A | 9/1999 | Roser et al. | |
| 5,965,161 A | 10/1999 | Oshlack et al. | |
| 5,965,163 A | 10/1999 | Miller et al. | |
| 5,969,181 A | 10/1999 | Breitenbach et al. | |
| 6,001,391 A | 12/1999 | Zeidler et al. | |
| 6,009,690 A | 1/2000 | Rosenberg et al. | |
| 6,027,747 A | 2/2000 | Terracol et al. | |
| 6,037,157 A | 3/2000 | Norbeck et al. | |
| 6,042,847 A | 3/2000 | Kerc et al. | |
| 6,045,829 A | 4/2000 | Liversidge et al. | |
| 6,051,253 A | 4/2000 | Zettler et al. | |
| 6,063,821 A | 5/2000 | Breitenbach et al. | |
| 6,066,334 A | 5/2000 | Kolter et al. | |
| 6,071,539 A | 6/2000 | Robinson et al. | |
| 6,083,518 A | 7/2000 | Lindahl | |
| 6,113,941 A | 9/2000 | Takada et al. | |
| 6,120,802 A | 9/2000 | Breitenbach et al. | |
| 6,132,659 A | 10/2000 | Rosenberg et al. | |
| 6,136,346 A | 10/2000 | Eljamal et al. | |
| 6,150,424 A | 11/2000 | Breitenbach et al. | |
| 6,162,467 A | 12/2000 | Miller et al. | |
| 6,187,342 B1 | 2/2001 | Zeidler et al. | 424/486 |
| 6,197,781 B1 | 3/2001 | Guitard et al. | |
| 6,207,197 B1 | 3/2001 | Illum et al. | |
| 6,221,368 B1 | 4/2001 | Breitenbach et al. | |
| 6,221,399 B1 | 4/2001 | Rolfes et al. | |
| 6,221,400 B1 | 4/2001 | Liversidge et al. | |
| 6,232,333 B1 | 5/2001 | Lipari et al. | |
| 6,248,363 B1 | 6/2001 | Patel et al. | |
| 6,251,434 B1 | 6/2001 | Breitenbach et al. | |
| 6,261,599 B1 | 7/2001 | Oshlack et al. | |
| 6,264,981 B1 | 7/2001 | Zhang et al. | |
| 6,271,307 B1 | 8/2001 | Huff et al. | |
| 6,274,727 B1 * | 8/2001 | Maul et al. | 536/127 |
| 6,281,282 B1 | 8/2001 | Breitenbach et al. | |
| 6,284,270 B1 | 9/2001 | Lagoviyer et al. | |
| 6,284,803 B1 | 9/2001 | Kothrade et al. | |
| 6,290,990 B1 * | 9/2001 | Grabowski et al. | 424/499 |
| 6,294,192 B1 | 9/2001 | Patel et al. | |
| 6,312,726 B1 | 11/2001 | Nakamichi et al. | |
| 6,318,650 B1 | 11/2001 | Breitenbach et al. | |
| 6,319,520 B1 | 11/2001 | Wuthrich et al. | |
| 6,322,816 B1 | 11/2001 | Zeidler et al. | |
| 6,333,048 B1 | 12/2001 | Asmussen et al. | |
| 6,350,398 B1 | 2/2002 | Breitenbach et al. | |
| 6,372,259 B1 | 4/2002 | Kumar | |
| 6,372,905 B1 | 4/2002 | Chemburkar et al. | |
| 6,375,982 B1 | 4/2002 | Cherukuri | |
| 6,379,707 B2 | 4/2002 | Vladyka, Jr. et al. | |
| 6,383,471 B1 | 5/2002 | Chen et al. | |
| 6,387,401 B2 | 5/2002 | Rosenberg et al. | 424/464 |
| 6,391,338 B1 | 5/2002 | Frisbee et al. | |
| 6,423,256 B1 | 7/2002 | Kothrade et al. | |
| 6,436,440 B1 | 8/2002 | Meffert et al. | |
| 6,440,946 B1 | 8/2002 | Kiso et al. | |
| 6,451,339 B2 | 9/2002 | Patel et al. | |
| 6,462,093 B1 | 10/2002 | Miyamoto et al. | |
| 6,465,010 B1 | 10/2002 | Lagoviyer et al. | |
| 6,465,011 B2 | 10/2002 | Law et al. | |
| 6,488,939 B1 | 12/2002 | Zeidler et al. | |
| 6,488,961 B1 | 12/2002 | Robinson et al. | |
| 6,488,963 B1 | 12/2002 | McGinity et al. | |
| 6,497,905 B1 | 12/2002 | Vladyka, Jr. et al. | |
| 6,511,681 B2 | 1/2003 | Vladyka, Jr. et al. | |
| 6,528,089 B1 | 3/2003 | Kothrade et al. | |
| 6,541,030 B2 | 4/2003 | Vaghefi | |
| 6,541,034 B1 | 4/2003 | Gergely et al. | |
| 6,547,997 B1 | 4/2003 | Breitenbach et al. | |
| 6,569,455 B1 | 5/2003 | Kanikanti et al. | |
| 6,576,255 B1 | 6/2003 | Petereit et al. | |
| 6,579,521 B2 | 6/2003 | Sahner | |
| 6,589,556 B2 | 7/2003 | Cherukuri | |
| 6,599,528 B1 * | 7/2003 | Rosenberg et al. | 424/451 |
| 6,599,931 B1 | 7/2003 | Breitenbach et al. | |
| 6,608,198 B2 | 8/2003 | Dickman et al. | |
| 6,610,764 B1 | 8/2003 | Martin et al. | |
| 6,632,389 B1 | 10/2003 | Ernst et al. | |
| 6,632,455 B2 | 10/2003 | Sangekar et al. | |
| 6,649,186 B1 | 11/2003 | Robinson et al. | |
| 6,669,879 B1 | 12/2003 | Spengler et al. | |
| 6,669,883 B1 | 12/2003 | Rosenberg et al. | |
| 6,677,362 B1 | 1/2004 | Ghebre-Sellassie et al. | |
| 6,692,767 B2 | 2/2004 | Burnside et al. | |
| 6,706,281 B2 | 3/2004 | Oshlack et al. | |
| 6,706,283 B1 | 3/2004 | Appel et al. | |
| 6,713,081 B2 | 3/2004 | Robinson et al. | |
| 6,730,319 B2 | 5/2004 | Maeder et al. | |
| 6,733,781 B2 | 5/2004 | Abu-Izza et al. | |
| 6,737,005 B1 | 5/2004 | Rosenberg et al. | |
| 6,743,442 B2 | 6/2004 | Oshlack et al. | |
| 6,763,607 B2 | 7/2004 | Beyernick et al. | |
| 6,787,157 B1 | 9/2004 | Rosenberg et al. | |
| 6,805,881 B1 | 10/2004 | Kanikanti et al. | |
| 6,834,310 B2 | 12/2004 | Munger et al. | |
| 6,872,336 B2 | 3/2005 | Tanno et al. | |
| 6,894,171 B1 | 5/2005 | Bauer et al. | |
| 6,899,899 B2 | 5/2005 | Takagi et al. | |
| 6,923,988 B2 | 8/2005 | Patel et al. | |
| 6,973,741 B2 | 12/2005 | Beyerinck et al. | |
| 6,982,094 B2 | 1/2006 | Sowden | |
| 7,014,810 B2 | 3/2006 | Krull et al. | |
| 7,022,344 B1 | 4/2006 | Kothrade et al. | |
| 7,122,143 B2 | 10/2006 | Sowden et al. | |
| 7,229,641 B2 | 6/2007 | Cherukuri | |
| 7,235,260 B2 | 6/2007 | Crew et al. | |
| 7,282,218 B2 | 10/2007 | Kulkarni et al. | |
| 7,297,345 B2 | 11/2007 | Sowden | |
| 7,407,670 B2 | 8/2008 | Six et al. | |
| 7,413,690 B1 | 8/2008 | Cheboyina et al. | |
| 7,419,685 B2 | 9/2008 | Kothrade et al. | |
| 7,491,407 B2 | 2/2009 | Pourdeyhimi et al. | |
| 7,550,158 B2 | 6/2009 | Appel et al. | |
| 7,645,474 B1 | 1/2010 | Pathak et al. | |
| 7,687,071 B1 | 3/2010 | Heger et al. | |
| 7,727,551 B2 | 6/2010 | Massironi | |
| 7,771,632 B2 | 8/2010 | Ghebre-Sellassie et al. | |
| 7,780,988 B2 | 8/2010 | Beyerinck et al. | |
| 7,785,512 B1 | 8/2010 | Pathak | |
| 7,846,477 B2 | 12/2010 | Rosenberg et al. | |
| 7,867,517 B2 | 1/2011 | Massironi | |
| 7,887,840 B2 | 2/2011 | Curatolo et al. | |
| 7,923,026 B2 | 4/2011 | Moschwitzer | |
| 7,951,401 B2 | 5/2011 | Colombo et al. | |
| 7,968,120 B2 | 6/2011 | Li et al. | |
| 7,972,624 B2 | 7/2011 | Li et al. | |
| 2001/0006650 A1 | 7/2001 | Burnside et al. | |
| 2001/0006677 A1 | 7/2001 | McGinity et al. | |
| 2001/0038852 A1 | 11/2001 | Kolter et al. | |
| 2001/0044409 A1 | 11/2001 | Ghebre-Sellassie et al. | |
| 2001/0048946 A1 | 12/2001 | Ghebre-Sellassie | |
| 2001/0051721 A1 | 12/2001 | Dickman et al. | |
| 2002/0001617 A1 | 1/2002 | Lee et al. | |
| 2002/0006443 A1 | 1/2002 | Curatolo et al. | |
| 2002/0009494 A1 | 1/2002 | Curatolo et al. | |

| | | | | | | |
|---|---|---|---|---|---|---|
| 2002/0015731 A1 | 2/2002 | Appel et al. | | 2008/0153925 A1 | 6/2008 | Pierobon et al. |
| 2002/0031547 A1 | 3/2002 | Takagi et al. | | 2008/0187612 A1 | 8/2008 | Kannar et al. |
| 2002/0044968 A1 | 4/2002 | Van Lengerich | | 2008/0199516 A1 | 8/2008 | McAllister |
| 2002/0102300 A1 | 8/2002 | Miller et al. | | 2008/0206349 A1 | 8/2008 | Barnwell et al. |
| 2002/0114833 A1 | 8/2002 | Abu-Izza et al. | | 2008/0206350 A1 | 8/2008 | Gryczke |
| 2002/0122825 A1 | 9/2002 | Hinrichs et al. | | 2008/0213371 A1 | 9/2008 | Jain et al. |
| 2002/0142043 A1 | 10/2002 | Kato et al. | | 2008/0241261 A1 | 10/2008 | Kolter et al. |
| 2002/0160042 A1 | 10/2002 | Petereit et al. | | 2008/0248107 A1 | 10/2008 | Pilgaonkar et al. |
| 2002/0161884 A1 | 10/2002 | Munger et al. | | 2008/0254124 A1 | 10/2008 | Bar-Shalom |
| 2003/0015814 A1 | 1/2003 | Krull et al. | | 2008/0260814 A1 | 10/2008 | Petereit et al. |
| 2003/0021842 A1 | 1/2003 | Lagoviyer et al. | | 2008/0260835 A1 | 10/2008 | Hayes et al. |
| 2003/0054038 A1 | 3/2003 | Crew et al. | | 2008/0305168 A1 | 12/2008 | Moon et al. |
| 2003/0059468 A1 | 3/2003 | Mattern et al. | | 2009/0017125 A1 | 1/2009 | Lynenskjold et al. |
| 2003/0064108 A1 | 4/2003 | Lukas et al. | | 2009/0036551 A1 | 2/2009 | Venkatesh et al. |
| 2003/0086976 A1 | 5/2003 | Hayes et al. | | 2009/0053317 A1 | 2/2009 | Vigo et al. |
| 2003/0091626 A1 | 5/2003 | Katsuta | | 2009/0104269 A1 | 4/2009 | Graham et al. |
| 2003/0099690 A1 | 5/2003 | Awamura et al. | | 2009/0148517 A1 | 6/2009 | Oshlack et al. |
| 2003/0099703 A1 | 5/2003 | Aoki | | 2009/0218731 A1 | 9/2009 | Rogasch et al. |
| 2003/0104065 A1 | 6/2003 | Brodin et al. | | 2009/0258953 A1 | 10/2009 | Dobrawa et al. |
| 2003/0104068 A1 | 6/2003 | Mathiowitz et al. | | 2009/0263479 A1 | 10/2009 | Moschwitzer et al. |
| 2003/0109639 A1 | 6/2003 | Lippold et al. | | 2009/0304795 A1 | 12/2009 | Bernigal et al. |
| 2003/0133984 A1 | 7/2003 | Ambühl et al. | | 2010/0010101 A1 | 1/2010 | Cherukuri |
| 2003/0141378 A1 | 7/2003 | Raehse et al. | | 2010/0062073 A1 | 3/2010 | Beyerinck et al. |
| 2003/0152619 A1 | 8/2003 | Stevens et al. | | 2010/0068268 A1 | 3/2010 | Rahmouni et al. |
| 2003/0153608 A1 | 8/2003 | Maegerlein et al. | | 2010/0112050 A1 | 5/2010 | Ryoo et al. |
| 2003/0161884 A1 | 8/2003 | Rosenberg et al. | | 2010/0137455 A1 | 6/2010 | Bouillo et al. |
| 2003/0203027 A1 | 10/2003 | Verreck et al. | | 2010/0166857 A1 | 7/2010 | Yan et al. |
| 2003/0206947 A1 | 11/2003 | Kanikanti et al. | | 2010/0172974 A1 | 7/2010 | Oshlack et al. |
| 2003/0211168 A1 | 11/2003 | Lynenskjold et al. | | 2010/0204259 A1 | 8/2010 | Tygesen et al. |
| 2003/0219489 A1 | 11/2003 | Curatolo et al. | | 2010/0204425 A1 | 8/2010 | Mertoglu et al. |
| 2004/0013697 A1 | 1/2004 | Berndl et al. | | 2010/0215753 A1 | 8/2010 | Sherwood et al. |
| 2004/0013734 A1 | 1/2004 | Babcock et al. | | 2010/0222220 A1 | 9/2010 | Hanna et al. |
| 2004/0013735 A1 | 1/2004 | Martin-Letellier et al. | | 2010/0247612 A1 | 9/2010 | Fuisz |
| 2004/0013736 A1 | 1/2004 | Nakano et al. | | 2010/0256110 A1 | 10/2010 | Babcock et al. |
| 2004/0014817 A1 | 1/2004 | Rosenberg et al. | | 2011/0020455 A1 | 1/2011 | Yoshida et al. |
| 2004/0029892 A1 | 2/2004 | Rosenberg et al. | | 2011/0091546 A1 | 4/2011 | Tanaka et al. |
| 2004/0044196 A1 | 3/2004 | Davidson et al. | | 2011/0123652 A1 | 5/2011 | Berndl et al. |
| 2004/0062778 A1 | 4/2004 | Shefer et al. | | 2011/0217381 A1 | 9/2011 | Angus et al. |
| 2004/0062802 A1 | 4/2004 | Hermelin | | 2011/0236443 A1 | 9/2011 | Hall et al. |
| 2004/0067256 A1 | 4/2004 | Juppo | | 2011/0244002 A1 | 10/2011 | Shen et al. |
| 2004/0076673 A1 | 4/2004 | Bateman et al. | | 2011/0250269 A1 | 10/2011 | Xu et al. |
| 2004/0081694 A1 | 4/2004 | Oshlack et al. | | 2011/0288181 A1 | 11/2011 | Koltzenburg et al. |
| 2004/0081701 A1 | 4/2004 | Erkoboni et al. | | 2012/0225953 A1 | 9/2012 | Berndl et al. |
| 2004/0110694 A1 | 6/2004 | Ghebre-Sellassie et al. | | | | |
| 2004/0115256 A1 | 6/2004 | MacAllister et al. | | | FOREIGN PATENT DOCUMENTS | |
| 2004/0120927 A1 | 6/2004 | Nathan | | CA | 2227272 A1 | 3/1997 |
| 2004/0138231 A1 | 7/2004 | Bateman et al. | | CA | 2232357 A1 | 5/1997 |
| 2004/0146550 A1 | 7/2004 | Ng et al. | | CA | 2343234 | 3/2000 |
| 2004/0151056 A1 | 8/2004 | Omtveit et al. | | CA | 2352874 | 6/2000 |
| 2004/0166153 A1 | 8/2004 | McAllister et al. | | CA | 2367020 | 9/2000 |
| 2004/0197414 A1 | 10/2004 | Ahola et al. | | CA | 2368625 | 10/2000 |
| 2004/0198901 A1 | 10/2004 | Graham et al. | | CA | 2374931 | 1/2001 |
| 2004/0219222 A1 | 11/2004 | Sjoblom | | CA | 2408915 | 11/2002 |
| 2004/0228916 A1 | 11/2004 | Tanno et al. | | CA | 2229650 C | 8/2006 |
| 2004/0247666 A1 | 12/2004 | Massironi | | DE | 973095 | 12/1959 |
| 2004/0265378 A1 | 12/2004 | Peng et al. | | DE | 19536387 A1 | 4/1997 |
| 2005/0014304 A1 | 1/2005 | Moon et al. | | DE | 19629753 A1 | 1/1998 |
| 2005/0042293 A1 | 2/2005 | Jackson et al. | | DE | 19637479 | 3/1998 |
| 2005/0048116 A1 | 3/2005 | Straub et al. | | DE | 99/00341 A1 * | 6/1999 |
| 2005/0058710 A1 | 3/2005 | Straub et al. | | DE | 9900341 A1 * | 6/1999 |
| 2005/0089568 A1 | 4/2005 | Oshlack et al. | | EP | 0240904 | 10/1987 |
| 2005/0100586 A1 | 5/2005 | Sournac et al. | | EP | 0240906 | 10/1987 |
| 2005/0100598 A1 | 5/2005 | Mizumoto et al. | | EP | 252886 A2 | 1/1988 |
| 2005/0169988 A1 | 8/2005 | Tao et al. | | EP | 0272336 | 6/1988 |
| 2005/0175687 A1 | 8/2005 | McAllister et al. | | EP | 0414422 A2 | 2/1991 |
| 2005/0281876 A1 | 12/2005 | Li et al. | | EP | 421582 A1 | 4/1991 |
| 2006/0051412 A1 | 3/2006 | Petereit et al. | | EP | 0435450 | 7/1991 |
| 2006/0115539 A1 | 6/2006 | Prasch | | EP | 0551820 | 7/1993 |
| 2006/0134203 A1 | 6/2006 | Ambuhl et al. | | EP | 0570327 | 11/1993 |
| 2006/0204577 A1 | 9/2006 | Crew et al. | | EP | 358105 B1 | 3/1994 |
| 2007/0014856 A1 | 1/2007 | Takagi et al. | | EP | 414422 B1 | 4/1994 |
| 2007/0042044 A1 | 2/2007 | Fischer et al. | | EP | 864324 A1 | 9/1998 |
| 2007/0077305 A1 | 4/2007 | Le et al. | | EP | 864326 A2 | 9/1998 |
| 2007/0098795 A1 | 5/2007 | Miller et al. | | EP | 988106 A1 | 3/2000 |
| 2007/0122482 A1 | 5/2007 | Holm et al. | | EP | 1003485 A1 | 5/2000 |
| 2007/0249692 A1 | 10/2007 | Fort et al. | | EP | 1027886 A2 | 8/2000 |
| 2007/0275058 A1 | 11/2007 | Tanaka et al. | | EP | 1027887 A2 | 8/2000 |
| 2008/0038340 A1 | 2/2008 | Kusaki et al. | | EP | 1070496 A1 | 1/2001 |
| 2008/0138419 A1 | 6/2008 | Liao et al. | | EP | 988106 B1 | 8/2001 |

| | | | |
|---|---|---|---|
| EP | 732923 B1 | 12/2001 | |
| EP | 942721 B1 | 1/2003 | |
| EP | 864324 B1 | 10/2003 | |
| EP | 852140 B1 | 12/2003 | |
| EP | 864326 B1 | 6/2004 | |
| EP | 2311435 A1 | 4/2011 | |
| GB | 2011382 A | 7/1979 | |
| GB | 2053681 A | 2/1981 | |
| GB | 2011382 B | 8/1982 | |
| GB | 2173703 A | 10/1986 | |
| JP | 61205208 A | 9/1986 | |
| KR | 1019075252 A | 10/1999 | |
| WO | WO8905138 A1 | 6/1989 | |
| WO | WO9006115 A2 | 6/1990 | |
| WO | WO9118613 A1 | 12/1991 | |
| WO | WO9307859 A1 | 4/1993 | |
| WO | WO9311749 A1 | 6/1993 | |
| WO | WO9315736 A1 | 8/1993 | |
| WO | WO9320138 A2 | 10/1993 | |
| WO | WO9507696 A1 | 3/1995 | |
| WO | WO9509614 A1 | 4/1995 | |
| WO | WO9522319 A1 | 8/1995 | |
| WO | WO 9528147 A1 | * 10/1995 | |
| WO | WO9600179 A1 | 1/1996 | |
| WO | WO9619962 A1 | 7/1996 | |
| WO | WO9619963 A1 | 7/1996 | |
| WO | WO9623499 A1 | 8/1996 | |
| WO | WO9636318 A2 | 11/1996 | |
| WO | WO9706781 A1 | 2/1997 | |
| WO | WO9713503 A1 | 4/1997 | |
| WO | WO9715291 A1 | 5/1997 | |
| WO | 97/34645 | 9/1997 | |
| WO | WO9744014 A1 | 11/1997 | |
| WO | WO9746222 A1 | 12/1997 | |
| WO | WO9807429 A2 | 2/1998 | |
| WO | WO9822094 A2 | 5/1998 | |
| WO | WO9824430 A1 | 6/1998 | |
| WO | WO9938496 A1 | 8/1999 | |
| WO | WO9955774 A1 | 11/1999 | |
| WO | WO9963841 A1 | 12/1999 | |
| WO | 00/0179 | 1/2000 | |
| WO | WO0040220 A1 | 7/2000 | |
| WO | WO0057854 A2 | 10/2000 | |
| WO | WO0100175 A1 | 1/2001 | |
| WO | WO0122938 A1 | 4/2001 | |
| WO | WO0123362 A2 | 4/2001 | |
| WO | WO0134118 A2 | 5/2001 | |
| WO | WO0134119 A2 | 5/2001 | |
| WO | WO0191727 A2 | 12/2001 | |
| WO | WO0203955 A1 | 1/2002 | |
| WO | WO0205788 A1 | 1/2002 | |
| WO | WO0235991 A2 | 5/2002 | |
| WO | WO0238126 A2 | 5/2002 | |
| WO | WO0245696 A1 | 6/2002 | |
| WO | WO02089835 A2 | 11/2002 | |
| WO | WO02092595 A1 | 11/2002 | |
| WO | WO03047551 A1 | 6/2003 | |
| WO | WO2007002041 A2 | 1/2007 | |
| WO | WO2007050631 A2 | 5/2007 | |
| WO | WO2010017053 A1 | 2/2010 | |
| WO | WO2011090724 A2 | 7/2011 | |
| WO | WO2011159626 A1 | 12/2011 | |
| ZA | 9608134 A | 3/1998 | |

OTHER PUBLICATIONS

Rodriguez Espinosa et al. "Dissolution kinetics for co-precipitates of diflunisal with PVP K30", Eur J Drug Metab Pharmacokinet. Apr.-Jun. 1998;23(2):109-12.*
Abu T. M. Sirajuddin, "Solid Dispersion of Poorly Water-Soluble Drugs: Early Promises, Subsequent Problems, and Recent Breakthroughs" Journal of Pharmaceutical Sciences, vol. 88, No. 10, Oct. 1999.*
Joseph B. Schwartz Pharmaceutical Dosage Forms, vol. 2, New York, Marcel Dekker, Inc., 1990 pp. 460-461.*
Bachynsky et al., *Drug Dev. and Ind. Phar.*, 23(8), 809-817, 1997.
Abu Serajuddin, *Journees Galeniques*, 43-49, 1997.
"Pharmazeuitische Technologie" Published by Ullstein Mosby, 7th Edition, 1993, pp. 80-85.
Serajuddin, A.T.M, "Solid Dispersioin of Poorly Water-Soluble Drugs: Early Promises, Subsequent Problems, and Recent Breakthroughs," J. of Pharm. Sci., 1999, vol. 88 (10), pp. 1058-1066.
Aungst B.J. et al., "Improved Oral Bioavailability of an HIV Protease Inhibitor Using Gelucire 44/14 and Labrasol Vehicles," vol. 87, pp. 49-54, 1994.
Aungst et al., "Amphiphilic vehicles improve the oral bioavailability of a poorly soluble HIV protease inhibitor at high doses," International Journal of Pharmaceutics, vol. 156, pp. 79-88, 1997.
BASF Fine Chemicals, "ExAct Excipients & Actives fa Pharma", BASF, 2:1-16 (1999).
Breitenbach Jorg et al., "Confocal Raman-Spectroscopy: Analytical Approach to Solid Dispersions and Mapping of Drugs," Pharm. Research, vol. 16 (7), pp. 1109-1113, 1999.
Center for Drug Evaluation and Research, Chemistry Reviews, 1999.
Chiou, W.L. et al., "Pharmaceutical Applications of Solid Dispersion Systems," J. of Pharm. Sci., vol. 60 (9), pp. 1281-1302, 1971.
Corrigan et al., "Amorphous forms of thiazide diuretics prepared by spray-drying," International Journal 01 Pharmaceutics, 1984, pp. 195-200, vol. 18.
Corrigan et al., "Amorphous spray-dried hydrofiumethiazide-polymiylpyrrolidone systems: physicochemical properties," J. Pharm. Pharmacol, 1984, pp. 217-221, vol. 36.
Corrigan et al., "Physicochemical Properties of Spray Dried Drugs: Phenobarbitone and Hydroflumethiazide," Drug Development and Industrial Pharmacy, 1983, pp. 1-20, vol. 9 (1&2).
Dias L. et al., "Physical and Oral Drug Bioavailability Evaluations of ABT-538: PVP Co-Precipitates' Poster," Physical Research Suppl. (0724-8741), vol. 13 (9), pp. S-351 PDD7475, 1996.
Ford J. L., "The Current Status of Solid Dispersions," Pharm. Acta Helv, 1986, 61 (3), 69-88.
Formulation Technology, Emulsions, Suspensions, Solid Forms, Wiley-VCH, 2001, pp. 358-374.
Hajratwala et al., "Effect of Aging on Hydrocortisone-Polyet hylene Glycol 4000 and Hydrocortisone-Polyvinylpyrrolidone Dispersions," Journal of Pharmaceutical Sciences, 1984, pp. 1539-1541, vol. 73 (11).
Hancock et al., "Characteristics and Significance of the Amorphous State in Pharmaceutical Systems," Journal of Pharmaceutical Sciences, 1997, pp. 1-12, vol. 86 (1).
Hancock et al., "Molecular Mobility of Amorphous Pharmaceutical Solids Below Their Glass Transition Temperatures," Pharmaceutical Research, 1995, pp. 799-806, vol. 12 (6).
Hasegawa et al., "Application of Solid Dispersions with Enteric Coating Agents to Overcome Some Pharmaceutical Problems," Chem. Pharm. Bull, 1986, pp. 2183-2190, vol. 34 (5).
Hasegawa et al., "Physical Properties of Solid Dispersions of Poorly Water-Soluble Drugs with Enteric Coating Agents1)," Chem. Pharm. Bull, 1985, pp. 3429-3435, vol. 33 (8).
Hasegawa et al., "Solid Dispersicn Obtained from Nifedipine and Enteric Coaling Agent. 1. Dissoluticn Behavicr," 1984, pp. 485-489, vol. 104.
Hasegawa et al., "Supersaturation Mechanism of Drugs from Solid Dispersions with Enteric Coating Agents," Chem. Pharm. Bull, 1988, pp. 4941-4950, vol. 36 (12).
Hulsmann S. et al., "Melt extrusion—an alternative method for enhancing the eissolution rate of 17.beta.-estradiol hemihydrate," Eur. J. of Pharm. & Biopharm, vol. 49, pp. 237-242, 2000.
Jachowicz et al., "Solid dispersions of oxazepam," International Journal of Pharmaceutics, 1993, pp. 321-325, vol. 99.
Leuner C., et al., "Improving drug solubility for oral delivery using solid dispersions," European Journal of Pharmaceutics and Biopharmaceutics, 2000, 50, 47-60.
Martin D. et al., "Method of Preparing an Orally Bioavailable Solid Formulation of an Insoluble Protease Inhibitor as a Coprecipitate With PVP and Other Excipients," Pharmaceutical Research Suppl., vol. 13 (9), p. S351 PDD 7474, 1996.
Mueller, "Badische Anilin- und Soda-Fabrik AG, Ludwigshafen/ Rhein Untersuchungslaboratorium, Nachweis und Bestimmung von Polyvinylpyrrolidon (PVP) sowie Bestimmung von Wirkstoffen in PVP-haltigen Arzneimittelzubereitungen," Tica Acta Helvetiae, 1968, pp. 107-122, vol. 43.

Nakamichi Kouichi et al., "Preparation of Nifedipine-Hydroxypropylmethylcellulose Phthalate Solid Dispersion by Twin Screw Extruder and its Evaluation," Yakuzaigaku, 1996, pp. 15-22, vol. 56 (1).

Otsuka et al., "Hygroscopic Stability and Dissolution Properties of Spray-Dried Solid Dispersions of Furosemide with Eudragit," Journal of Pharmaceutical Sciences, 1993, pp. 32-38, vol. 82(1).

Palmieri, G.F. et al., "Characterization and dissolution studies of PEG 4000/fenofibrate solid dispersions," S.T.P. Pharma Sci, vol. 6 (3), pp. 188-194 (1996).

Peltonen et al., "Surface Pressure, Hysteresis, Interfacial Tension, and CMC of Four Sorbitan Monoesters at Water•Air, Water•Hexane, and Hexane•Air Interfaces," Journal of Colloid and Interface Science, 2000, pp. 1-6, vol. 227.

Saleki-Gerhardt et al., "Non-Isothermal and Isothermal Crystallization of Sucrose from the Amorphous State," Pharmaceutical Research, 1994, pp. 1166-1173, vol. 11 (8).

Shamblin et al., "The Effects of Co-Lyophilized Polymeric Additives on the Glass Transition Temperature and Crystallization of Amorphous Sucrose," Journal of Thermal Analysis, 1996, pp. 1567-1579, vol. 47.

Simonelli et al., "Dissolution Rates of High Energy Polyvinylpyrrolidone (PVP) Sulfathiazole Coprecipitates," Jourirul of Pharmaceutical Sciences, 1969, pp. 538-549, vol. 58 (5).

Takeuchi et al., "Spherical Solid Dispersion Containing Amorphous Tolbutamide Embedded in Enteric Coating Polymers or Colloid al Silica Prepared by Spray-Drying Technique," Chem. Pharm. Bull, 1987, pp. 3800-3806, vol. 35 (9).

Teas, "Graphic Analysis of Resin Solubilities," Journal of Paint Technology, 1968, pp. 19-25, vol. 40 (516).

Vandenmooter, G. et al., "Physical stabilisation of amorphous ketoconazole in solid dispersions with polyvinylpyrrolidone K25," European Journal of Pharmaceutical Sciences, 2001, pp. 261-269, vol. 12.

Voigt R., et al., "Methods for determination of wett ability and their possible use in pharmaceutical technology", Pharmazie, 1975, 30 (11), 689-93.

Yamagochi et al., "Improvement of Pharmaceutical Properties of 4"-O- (4-methoxyphenyl)acetyltylosin Using Solid Dispersion with Carboxymethylethylcellulose," Yakuzaigaku, 1993, pp. 221-228, vol. 53 (4).

Yu Lian, "Amorphous pharmaceutical solids: preparation, characterization and stabilization," Advanced Drug Delivery Reviews, 2001, pp. 27-42, vol. 48.

Voigt R., "Pharmaceutical Technology" for Students and Professionals, 7th revised Edition, 2000, pp. 80-85.

Niazi S.K., "Handbook of Pharmaceutical Manufacturing Formulations, Compressed Solid Products" 2004, vol. 1, CRC Press, pp. 60-101.

Office Action for U.S. Appl. No. 12/899,227, filed Oct. 6, 2010 dated Oct. 12, 2011.

Dias L., et al., "Physical and Oral Dog Bioavailability Evaluation of ABT-538: PVP Co-precipitates," 1996, PDD 7475, pp. S351.

Martin D., et al., "Method of Preparing an Orally Bioavailable Solid Formulation of an Insoluble Protease Inhibitor as a Coprecipitate with PVP and Other Excipients," Pharmaceutical Research Supply, 1996, vol. 13 (9), pp. S351 PDD 7474.

Forster, A., et al., "Characterization of Glass Solutions of Poorly Water-Soluble Drugs Produced By Melt Extrusion with Hydrophilic Amorphous Polymers," 2001, vol. 53 (3), pp. 303-315.

Herausgeber, "Chemistry" Georg Thieme Verlag Stuttgart—New York, 1997, pp. 1549.

Kaletra 2000.

Kolter K., et al., "Hot-Melt Extrustion with BASF Pharma Polymers Extrusion Compendium," BASF—The Chemical Company, 2010, pp. 34-35.

Polymer Handbook, Brandrup J., et al., Eds., Interscience Publishers, 1975, Table of Contents.

Rosenberg J., et al., "Meltrex-Formulations Containing Solid Solutions of Nearly Insoluble Drugs: Formation of Nanoparticles on Dissolution In Water," 28th International Symposium on Controlled Release of Bioactive Materials, 2001, vol. 1, pp. 738-739.

Sjokvist E., et al., "Physicochemical Aspects of Drug Release, XIII. The effect of sodium dodecyl sulphate additions on the structure and Dissolution of a drug in solid dispersions," International Journal of Pharmaceutics, 1991, vol. 69, pp. 53-62.

Vadnere M.K., "Coprecipitates and Melts" in: Encyclopedia of Pharmaceutical Technology, 2nd Edition, Swarbrick J., eds., Marcel Dekker, Inc, 2002, vol. 1, pp. 641-648.

Amastasiadou C., et al., "Solid Dispersions: Comparison of Prepared Melts and Coprecipitates of Diazepam and Polyoxyethylene Glycol 4000," Drug Development and Industrial Pharmacy, 1983, vol. 9 (1-2), pp. 103-115.

Bates T.R., "Dissolution Characteristics of Reserpine-Polyvinylpyrrolidone Co-Precipitates" in: Journal of Pharmacology, Letters to the Editor, 1969, vol. 21, pp. 710-712.

Chatham S.M., "The Use of Bases in SSM Formulations," S.T.P. Pharma Pratiques, 1987, vol. 3 (7), pp. 575-582.

Chiang C.C., et al., "Formulation Development of an Oral Dosage Form for an HIV Protease Inhibitor, Ag1284," International Journal of Pharmaceutics, 1995, vol. 117 (2), pp. 197-207.

Craig D.Q., et al., "The Relevance of the Amorphous State to Pharmaceutical Dosage Forms: Glassy Drugs and Freeze Dried Systems," International Journal of Pharmaceutics, 1999, vol. 179 (2), pp. 179-207.

Datta S., et al., "Crystal Structures of Drugs: Advances in Determination, Prediction and Engineering," Nature Reviews Drug Discovery, 2004, vol. 3 (1), pp. 42-57.

Fernandez M., et al., "Characterization of Solid Dispersions of Piroxicam/Polyethylene Glycol 4000," International Journal of Pharmaceutics, 1992, vol. 84 (2), pp. 197-202.

Fernandez M., et al., "Dissolution Kinetics of Piroxicam in Solid Dispersions with Polyethylene Glycal 4000," International Journal of Pharmaceutics, 1993, vol. 98 (1-3), pp. 23-35.

Gidwani R., et al., "Spray-Dried Enteric Solid Dispersion as a Novel Oral Delivery System for a Pentapeptide Analog of Thymopentin," Drug Development and Industry Pharmacy, 1992, vol. 18 (4), pp. 385-394.

Kempf D.J., et al., "Abt-538 Is A Potent Inhibitor of Human Immunodeficiency Virus Protease and has High Oral Bioavailability in Humans," Proceedings of the National Academy of Sciences USA, 1995, vol. 92 (7), pp. 2484-2488.

Longer, M., et al., "Preformulation Studies of a Novel HIV Protease Inhibitor, AG1343," Journal of Pharmaceutical Sciences, 1995, vol. 84 (9), pp. 1090-1093.

Serajuddin A.T., et al., "Effect of Vehicle Amphiphilicity on the Dissolution and Bioavailability of a Poorly Water-Soluble Drug from Solid Disperions," Journal of Pharmaceutical Sciences, 1988, vol. 77 (5), pp. 414-417.

Serajuddin A.T., et al., "Improved Dissolution of a Poorly Water-Soluble Drug from Solid Dispersions in Polyethylene Glycol: Polysorbate 80 Mixtures," Journal of Pharmaceutical Sciences, 1990, vol. 79 (5), pp. 463-464.

Sethia S., et al., "Solid Dispersions: Revival with Greater Possibilities and Applications in Oral Drug Delivery," Critical Reviews in Therapeutic Drug Carrier Systems, 2003, vol. 20 (2-3), pp. 215-247.

Sham H.L., et al., "ABT-378, A Highly Potent Inhibitor of the Human Immunodeficiency Virus Protease," Antimicrobial Agents and Chemotherapy, 1998, vol. 42 (12), pp. 3218-3224.

Stanley J.P., "Soft Gelatin Capsules" in: The Theory and Practice of Industrial Pharmacy, 3rd Edition, Lachman L., et al., Lea and Febiger, 1986, pp. 398-412.

Taylor L.S., et al., "Spectroscopic Characterization on Interactions Between PVP and Indomethacin in Amorphous Molecular Dispersions," Pharmaceutical Research, 1997, vol. 14 (12), pp. 1691-1698.

Yoshioka M., et al., "Inhibition of Indomethacin Crystallization in Poly(vinylpyrrolidone) Coprecipitates," Journal of Pharmaceutical Sciences, 1995, vol. 84 (8), pp. 983-986.

* cited by examiner

SELF-EMULSIFYING ACTIVE SUBSTANCE FORMULATION AND USE OF THIS FORMULATION

The present invention relates to self-emulsifying formulations based on an active ingredient component and a formulation base with a lipid component and with a binder component; to the use of this formulation as dosage form in the life science sector; the invention also describes a process for producing self-emulsifying formulations by mixing the formulation components to form a plastic mixture and, where appropriate, to manufacture the formulations as dosage form; and the use of a formulation base in the application of at least one active ingredient in the life science sector.

It is often desired to be able to employ active ingredients in emulsified form. Thus, in the pharmaceutical technology sector, active ingredients of low solubility are formulated together with selected excipients in order to ensure adequate absorption of the active ingredient for example in the gastrointestinal tract. These normally comprise nonionic surfactants with quite high HLB values, e.g. Cremophor®, Tween®, etc. This applies just as much to the drugs sector as to the crop protection sector.

For example, in WO 00/00179 oils or fats are emulsified or microemulsified with the addition of conventional emulsifiers, and active ingredients of low solubility in water are then incorporated into these emulsions or microemulsions.

Although these excipients are commonly designated chemically inert, they are known to have disadvantages which may become evident in particular at higher dosages through local and/or systemic toxicity.

Besides local irritation, it is not possible to preclude unwanted side effects of these substances derived from uptake of these solubilizers by an organism.

Emulsions, for example for parenteral administration, normally use emulsifying phospholipids, in particular lecithins. However, because of the inadequate chemical stability of the phospholipids, these emulsions may be associated with considerable storage stability problems. In addition, the preparation of such emulsions is complicated. Thus, it may be necessary to homogenize the phospholipids in water together with other emulsion constituents, for example lipids or lipid derivatives, under high pressure, i.e. under several 100 bar.

Besides the liquid emulsions described above, "solid" emulsions are also known. These formulations are generally referred to as self-emulsifying systems because they dissolve in aqueous systems to form an emulsion (cf. M. O. Bachynsky et al., "Factors Affecting the Efficiency of a Self-Emulsifying Oral Delivery System", Drug Development and Industrial Pharmacy, 23 (8), (1997) 809-816; U.S. Pat. No. 5,858,401). The solubilization-promoting excipients discussed at the outset are also mainly used in these cases, which entails the known disadvantages. Besides the low molecular weight surfactants, e.g. Tween®, which are particularly used, self-emulsifying systems based on polymeric glyceride surfactants are also described (A. T. M. Serajuddin, "Bioavailability Enhancement of poorly Water-Soluble Drugs by Solid Dispersion in Surface Active and Self-Emulsifying Vehicles", Bulletin Technique Gattefossé, No.90, (1997), pp. 43-50). These polymeric glycerides may act as surfactant because of their high HLB values (e.g. Gelucire® 44/14 with an HLB of 14). Because of their semisolid consistency, many of these formulations must be packed into gelatin capsules. This applies in particular to the use of the usually low-melting glyceride surfactants.

The object on which the present invention is based, of providing self-emulsifying dosage forms, is surprisingly achieved by formulations whose formulation base comprises a lipid component and a binder component.

The present invention therefore relates to self-emulsifying formulations based on i) at least one active ingredient and a formulation base with
ii) a lipid component;
iii) a binder component; and
iv) where appropriate other excipients.

The term "formulation" means in the framework of the present invention a mixture composed of components i), ii), iii) and, where appropriate, iv).

Active ingredients mean for the purpose of the invention all substances with a physiological effect. They are, in particular, active pharmaceutical ingredients (for humans and animals in the human and veterinary medical sectors), active ingredients for plant treatment, insecticides, active ingredients for human and animal food, fragrances, flavorings and perfumed oils. The amount of active ingredient per dose unit and the concentration may vary within wide limits depending on the activity and the release rate. A condition is that they suffice to achieve the desired effect.

Active ingredients for the purpose of the invention also include vitamins and minerals. The vitamins include the vitamins of the A group, the B group, which are meant besides $B_1$, $B_2$, $B_6$ and $B_{12}$ and nicotinic acid and nicotinamide to include also compounds with vitamin B properties such as adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purpose of the invention also include therapeutic peptides. Plant treatment agents include, for example, vinclozolin, epoxiconazole and quinmerac.

Active pharmaceutical ingredients include, for example: acebutolol, acetylcysteine, acetylsalicylic acid, acyclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkoniumhydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazolin, cefixime, cefotaxime, ceftazidime, ceftriaxone, cefuroxime, selegiline, chloramphenicol, chlorhexidine, chlorpheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphene, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxocyclin, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavinmononucleotide, fluconazole, flunarizine, fluorouracil, fluoxetine, flurbiprofen, furosemide, gallopamil, gemfibrozil, gentamicin, Gingko biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium-hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures or combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, pentoxifyllline, phenobarbital, phenoxymethylpenicillin, phenylephrine, phenylpropanolamine, phenytoin, piroxicam, polymyxin B, povidone-iodine, pravastatin, prazepam, prazosin, prednisolone, prednisone, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone-acetonide, triamterene, trimethoprim, troxerutin, uracil, valproic acid, vancomycin, verapamil, vitamin E, folinic acid, zidovudine.

The active ingredients which can be used according to the invention also include a large number of essential oils (aetheroleum), such as angelica oil (angelicae aetheroleum), anise oil (anisi aetheroleum), arnica oil (arnicae aetheroleum), aurantii aetheroleum, valerian oil (valerianae aetheroleum), basilici aetheroleum, bergamot oil (bergamottae aetheroleum), savory oil, bucco aetheroleum, camphor (camphora), cardamomi aetheroleum, cassia oil, chenopodium oil (chenopodii aetheroleum), chrysanthemum oil (pyrethri aetheroleum), cinae aetheroleum, citronella oil, lemon oil (limonis aetheroleum), citrus oil (citri aetheroleum), costus oil, curcuma oil (curcumae aetheroleum), carlina oil (carlinae aetheroleum), elemi oil, tarragon oil, eucalyptus oil (eucalypti aetheroleum), fennel oil (foeniculi aetheroleum), pine needle oil (piceae aetheroleum), pine oil, filicis aetheroleum, galbanum oil, gaultheriae aetheroleum, geranium oil, guaiac wood oil (guaiaci aetheroleum), hazelwort oil (asari aetheroleum), iris oil (iridis aetheroleum), hypericum oil (hyperici aetheroleum), calamus oil, camomile oil (e.g. chamomillae romanae aetheroleum; matricariae aetheroleum), fir needle oil (pini aetheroleum), garlic oil (allii sativi aetheroleum), coriander oil (coriandri aetheroleum), carraway oil (carvi aetheroleum), lauri aetheroleum, lavender oil (lavandulae aetheroleum), lemon grass oil, lovage oil (levistici aetheroleum), bay oil, lupuli strobuli aetheroleum, mace oil, marjoram oil (majoranae aetheroleum), mandarine oil, melissa oil (melissae aetheroleum; calaminthae aetheroleum), menthol (mentholum), millefolii aetheroleum, mint oil (menthae arvensis aetheroleum), clary oil, nutmeg oil (myristicae aetheroleum), spikenard oil (e.g. from Nardostachys jatamansi), clove oil (caryophylli aetheroleum), neroli oil, niaouli, olibanum oil, ononidis aetheroleum, opopranax oil, orange oil, oregano oil, orthosiphon oil, patchouli oil, parsley oil (petroselinum aetheroleum), petit-grain oil, peppermint oil (menthae piperitae aetheroleum), tansy oil (tanaceti aetheroleum), rosewood oil, rose oil, rosemary oil (rosmarini aetheroleum), rue oil (rutae aetheroleum), sabinae aetheroleum, saffron oil (croci aetheroleum), sage oil (salviae aetheroleum), sandalwood oil (santali aetheroleum), sassafras oil (sassafras aetheroleum), celery oil (apii aetheroleum), mustard oil (senapsis aetheroleum), serphylli aetheroleum, immortelle oil (e.g. from Helichrysum italicum), fir oil, teatree oil, terpentine oil (terebinthinae aetheroleum), thyme oil (thymi aetheroleum), juniper oil (juniperi aetheroleum), frankincense oil, hyssop oil (e.g. Hyssopus officinalis var. decumbens), cedar wood oil, cinnamon oil (cinnamomi aetheroleum), cypress oil.

Some of the aforementioned essential oils can also be used as insecticides, e.g. chrysanthemum oil and calamus oil, or as repellents, e.g. cassia oil, camphor, terpentine oil, citronella oil, cinnamon oil and clove oil.

The essential oils are usually mixtures of substances. Components of the mixture which should be particularly mentioned are terpene compounds, e.g monoterpenes, sesquiterpenes, and biterpenes and triterpenes, phenylpropane derivatives, simple phenols and their ethers, phenolcarboxylic acids, straight-chain hydrocarbons and their derivatives, short-chain acids, sulfur-containing compounds, e.g. mustard oils, and nitrogen-containing substances, e.g. indole derivatives and anthranilic esters.

In the true sense, the term "essential oil" means mixtures of substances which are obtainable from plant raw materials by steam distillation. Oils of this type can be obtained, depending on the amount and nature of the oil and depending on the plant raw material employed to obtain it, by oil extraction processes (enfleurage process), solvent extraction, pressing processes and other mechanical processes, and distillation processes, which include steam distillation. The oils obtained in this way can be subjected to further purification. This is advantageous in particular with steam-distilled oils and particularly expedient with a view to the pharmaceutical or cosmetic applications.

Active component i) in the formulations of the invention contains at least one active ingredient, in particular one of those aforementioned, and it may contain other active ingredients, to be selected in particular from those aforementioned, of the same or a different type.

A special type of active ingredient within the framework of the present invention is to be included, because of its fat-like nature, among the lipids, where appropriate also as lipid derivative or lipid-containing mixture. Active ingredients of this type are referred to hereinafter as lipid-like active ingredients. Statements concerning lipids also refer to such lipid-like active ingredients. The lipid-like active ingredients which can be used according to the invention are, in particular, oils and, especially, the aforementioned essential oils. This type of active ingredient may form a part or the entirety both of active ingredient component i) and of lipid component ii). In a particular aspect, therefore, the present invention relates to self-emulsifying formulations based on i') at least one lipid-like active ingredient and, where appropriate, other active ingredients and a formulation base with ii') where appropriate another lipid component cont nt;

iii) a binder component; and iv) where appropriate other excipients.

Accordingly, component i') comprises the active ingredient component i) and at least part of the lipid component ii); and component ii') comprises the part of lipid component ii) which is not comprised by i'). In a specific embodiment of this aspect, component i') comprises active ingredient component i) and lipid component ii), with the consequence that component ii') is not present. The component i') comprises at least one lipid-like active ingredient, i.e. it may also comprise two or more of these lipid-like active ingredients or else one or more other active ingredients. In another specific embodiment of this aspect, component i') consists of at least one lipid-like active ingredient.

Accordingly, the term "lipid component" refers—unless otherwise indicated—generally to component ii) and specifically, for example, to the lipid content of component i'), where appropriate in combination with component ii').

The formulations of the invention are particularly advantageous for those active ingredients which profit from the solubilizing property of the emulsions resulting when the formulations are dissolved in aqueous media. These are, in particular, active ingredients of low solubility, in particular those for which at least 100, in particular at least 1 000 parts, and preferably at least 10 000 parts of water are necessary to dissolve one part of active ingredient, but also active ingredients which are freely soluble in water but display only inadequate effects with certain ode of administration.

The active ingredient component i) usually constitutes 0.1 to 50% by weight, preferably 1 to 30% by weight, and in particular 5 to 20% by weight, of the formulation. Data in % by weight relate, unless otherwise indicated, to the total weight of the formulation.

The formulation base of formulations of the invention comprises excipients, namely in one embodiment at least one lipid, at least one binder and, where appropriate, other excipients and, in another embodiment in which the active ingredient component comprises at least one lipid-like active ingredient, comprises at least one binder and, where appropriate, other lipids and/or other excipients.

The lipid component of solid formulations of the invention comprises at least one lipid, which is intended to refer also to lipid derivatives and lipid-containing mixtures.

The term lipid is a collective designation for fats and fat-like substances. The similarity to fats is defined in particular by the solubility characteristics. Accordingly, fat-like substances such as fats themselves are, for example, practically insoluble in water. Substances are insoluble in water in the sense of the invention especially when at least 1 000 to 10 000 parts, and preferably at least 10 000 parts of water are necessary to dissolve one part of substance. They are also referred to as lipophilic or hydrophobic.

In one embodiment of the present invention, preferred lipids are those which an organism can assimilate, that is to say, for example, can take up and, where appropriate, metabolize. In this sense, those lipids and lipid derivatives which can be taken up via the gastrointestinal tract implement a particular embodiment of the present invention, in particular within the framework of pharmaceutical applications. Natural lipids and derivatives of natural lipids, which may be of vegetable or animal origin, are preferred.

Particularly within the framework of pharmaceutical applications, at least one lipid of the lipid component is preferably selected from endogeneous lipids. The endogeneous lipids include in particular lipids which are based on fatty acids with an even number of carbon atoms, in particular corresponding glycerides and fatty acids or derivatives thereof.

The term fatty acid refers to a group of aliphatic saturated or unsaturated carboxylic acids. The chains are usually unbranched and have 6 to 30, preferably 8 to 22, and in particular 8 to 18, carbon atoms. The saturated fatty acids include, for example, caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, behenic acid, lignoceric acid, cerotic acid and melissic acid. The unsaturated fatty acids may be unsaturated one or more times, in particular unsaturated once, twice, three times, four times, five times or six times. Examples of singly unsaturated fatty acids include palmitoleic acid, oleic acid and erucic acid, of doubly unsaturated fatty acids include sorbic acid and linoleic acid, of triply unsaturated fatty acids include linolenic acid and eleostearic acid, of quadruply unsaturated fatty acids include arachidonic acid, of quintuply unsaturated fatty acids include clupanodonic acid, and of sextuply unsaturated fatty acids include docosahexaenoic acid.

Singly or multiply unsaturated fatty acids are preferred, especially oleic acid, palmitoleic acid, erucic acid, linoleic acid, linolenic acid.

The term glycerides refers to esters of glycerol. Depending on the number of ester groups, reference is made to mono-, di- and triglycerides. The acid residue in a monoglyceride may be at position 1 or 2 and the acid residues of di- and triglycerides may be identical or different and be distributed in every conceiveable way over the three possible positions of glycerol. The acid residues are preferably the fatty acids described above. Examples of monoglycerides include glycerol monobehenate, glycerol monocaprate, glycerol monococoate, glycerol monoerucate, glycerol monoisostearate, glycerol monolanolate, glycerol monolaurate, glycerol monolinoleate, glycerol monomyristate, glycerol monooleate, glycerol monopalmitate, glycerol monoricinoleate, glycerol monostearate, of the diglycerides include glycerol dicaprylate, glycerol dilaurate, glycerol dimyristate, glycerol dioleate, glycerol dipalmitate and glycerol distearate, of the triglycerides include glycerol tricaprylate, glycerol trilaurate, glycerol trimyristate, glycerol trioctanoate, glycerol trioleate, glycerol triricinoleate and glycerol tristearate.

Preference is given to mono-, di- and triglycerides with unsaturated fatty acid residues, in particular the fatty acid residues which can preferably be used according to the invention, especially glycerol monooleate, glycerol dioleate, glycerol trioleate.

The lipid component of formulations of the invention preferably comprises at least one of the lipids described above or a mixture of at least two of the lipids described above, and it may contain other lipids of this type and also of other types.

In one embodiment of the present invention, the lipid component consists of one of the lipids described above.

In another embodiment of the present invention, the lipid component consists of a lipid mixture of at least two of the lipids described above, in particular of a fatty acid mixture, a glyceride mixture or a fatty acid/glyceride mixture.

The derivatives of natural lipids, which may be of vegetable or animal origin, include in particular those natural lipids which have been chemically and/or physically treated. A suitable chemical treatment is, for example, hydrogenation of unsaturated fatty acids or fatty acid residues in glycerides. A suitable physical treatment is, for example, fractionation of natural lipid mixtures.

The lipids which can be used according to the invention also include lipid-containing natural substance extracts which, besides lipid, may also contain other constituents. Mention should be made here in particular of the lipids and lipid mixtures listed in relevant pharmacopoeias, and derivatives thereof, such as vegetable oils or animal fats, e.g. olive oil, castor oil, sesame oil, peanut oil, almond oil, linseed oil, cocoa butter, sunflower oil, medium chain-length triglycerides (triglycerida mediocatenalia), calcium behenate, glycerol monostearate, medium chain-length partial glycerides (partialglycerida mediocatenalia), longer-chain partial glycerides (partialglycerida longicatenalia), which may also, where appropriate, be hydrogenated or refined, such as hydrogenated castor oil or refined castor oil. Once again, lipids with a content of unsaturated fatty acids or fatty acid residues are preferred.

In a particular embodiment of the present invention, at least part of the lipid component is formed by at least one lipid-like active ingredient. Reference is made mutatis mutandis to the above statements concerning lipid-like active ingredients. A specific embodiment comprises formulations of the invention with a lipid component which consists of at least one lipid-like active ingredient, in particular the aforementioned oils and, especially, the essential oils.

In a particular embodiment, lipid component i) or the lipid content of component i'), where appropriate in combination with component ii'), has an HLB not exceeding 12, preferably not exceeding 8 and, in particular, not exceeding 5. The HLB system (hydrophilic lipophilic balance system) assigns numerical values to surface-active substances; the HLB values of lipophilic substances are low, and those of hydrophilic ones are higher (Fiedler, H. B., Lexikon der Hilfsstoffe für Pharmazie, Kosmetik, und angrenzende Gebiete, 4th edition, Aulendorf: ECV-Editio-Cantor-Verlag (1996)). In particular, lipid component ii) or the lipid content of component i'), where appropriate in combination with component ii'), is insoluble or of only low solubility in water. Accordingly, this embodiment can be implemented in particular with the aforementioned fatty acids and glycerides or oils and especially essential oils.

In another preferred embodiment, lipid component ii) or the lipid content of component i'), where appropriate in combination with component ii'), has a melting point not exceeding 50° C., preferably not exceeding 40° C. and, in particular, less than 30° C. Accordingly, this embodiment can be implemented in particular with fatty acids such as tridecanoic acid, lauric acid, elaeostearic acid, preferably undecanoic acid, capric acid, erucic acid, in particular pelargonic acid, caprylic acid, enanthic acid, caproic acid, isostearic acid, oleic acid, palmitoleic acid, linoleic acid, linolenic acid, arachidonic acid, clupanodonic acid and docosahexaenoic acid, and glycerides such as glycerol monolaurate, glycerol monolinoeate, glycerol monooleate, glycerol monopalmitate, glycerol monoricinoleate, glycerol dioleate, glycerol trioleate and glycerol triricinoleate, and with the aforementioned essential oils.

It is particularly preferred for at least part of lipid component ii) or of the lipid content of component i'), where appropriate in combination with component ii'), and at least part of the binder component to form a molecular dispersion in the formulations of the invention. If the lipid content is greater than the binder content, there is said to be a molecular dispersion of the binder in the lipid. The lipid content is preferably less than the binder content, in which case there is said to be a molecular dispersion of the lipid in the binder.

The term "molecular dispersion" is known to the skilled worker and essentially describes systems in which a substance, in the present case at least part and preferably the predominant part of the lipid or binder component, is homogeneously dispersed in a solvent. In such cases, the solvent usually forms a matrix which, according to the invention, is formed by the binder or lipid component or at least by a predominant part of the binder or lipid component. The content of lipid crystals in a formulation of the invention is usually below 12% and, in particular, below 5%. Statements concerning contents of crystals are bas d on the total amount of the respective component.

In a particular embodiment, molecular dispersion systems are solid, in which case they are referred to as solid solutions.

A formulation of the invention which is essentially free of lipid crystals represents a particular embodiment of the present invention. This state corresponds to the maximum possible homogenization of the lipid or binder in the matrix. There are no interfaces in the molecular dispersion system.

In another particular embodiment, at least part of the active ingredient component is in the form of a molecular dispersion. The content of active ingredient crystals in a formulation of the invention is usually less than 12% and, in particular, less than 5%. These formulations include, in particular, those which are essentially free of active ingredient crystals. This state corresponds to the maximum possible homogenization of the active ingredient in the formulation base.

Formulations of the invention which are essentially free of lipid and active ingredient crystals and, in particular, those in which there are essentially no crystalline contents of any constituent (essentially amorphous or crystal-free formulations) represent another particular embodiment of the present invention. This state corresponds to the maximum possible homogenization of the formulation components. There are no interfaces in a formulation which is a molecular dispersion.

Known analytical methods can be used to investigate the state of such molecular dispersions, in particular solid solutions, for example differential scanning calorimetry (DSC) or wide angle X-ray scattering measurements (WAXS measurements). The DSC analytical measurement of a molecular dispersion lacks the melting peak which occurs with the crystalline pure substance and is usually endothermic. Another possibility for identifying a molecular dispersion is the reduction in intensity and/or absence of typical X-ray diffraction signals in the WAXS analysis.

The content of the lipid component in the formulation is usually from 6 to 60% by weight, preferably 11 to 40% by weight, and in particular 16 to 25% by weight.

One criterion for establishing the optimal amount of lipid is the homogeneity of the formulation of the invention in the melt. Especially in relation to the upper limit, a homogeneous incorporation of the lipid into the melt without phase separation ought to be ensured.

In a particular embodiment of the present invention, the content of lipid component ii) or of the lipid content of component i'), where appropriate in combination with component ii'), based on the binder component, is not more than 40% by weight, preferably not more than 30% by weight, and in particular not more than 25% by weight.

The binder component of the formulations of the invention can also be understood as binder which at least partly forms a binder matrix, in particular a polymer matrix. Binders for the purpose of the invention are solid, meltable solvents. The binder matrix serves especially to take up, and in particular to dissolve, at least part of lipid component i) or of the lipid content of component i'), where appropriate in combination with component ii'). This preferably leads to the formation of molecular dispersions. In this regard, reference is made to the above statements in connection with the lipid component.

The binder component is preferably at least partly soluble or swellable in aqueous media, expediently under the conditions of use, that is to say in particular physiological conditions.

Aqueous media include, within the framework of the present description, water and mixtures of water and other components which contain at least 50% by weight, preferably at least 70% by weight, and in particular at least 90% by weight, of water. Aqueous media include in particular body fluids such as fluids in the digestive tract, e.g. gastric juice and intestinal juices, saliva, urine, feces fluid, wound discharge, effusions, amniotic fluid, puncture fluids, lymph and blood; beverages based on water, such as tea, coffee, soft drinks or babyfood, food for parenteral nutrition, juices, syrups, water used for various purposes, for example in animal feeding and for watering plants, and for controlling pests, water for use in cleaning processes, e.g. for laundering or dishwashing, bath water, aqueous vehicles for use in formulations in the drugs, cosmetics or plant treatment sector, e.g. vehicles which can be administered parenterally, ointment, cream, paste or gel bases, water or aqueous media for use in aromatherapies or for inhalation.

Swelling means essentially a process in which the volume and/or shape of a solid body, for example a solid formulation of the invention, change on exposure to liquids, vapors and gases. Swellable or soluble applies in particular to hydrophilic polymers able to accumulate water at least on the surface and/or take up water between the polymer chains, mainly by absorption. Limited swelling usually results in gel formation, which is why polymers capable of limited swelling and usable according to the invention can be selected from the polymers commonly known as gel formers. Unlimited swelling usually leads to the formation of solutions or colloidal solutions, which is why polymers capable of unlimited swelling and usable according to the invention can be selected from the polymers which form at least colloidal solutions in the respective aqueous medium. It must be taken into account, for pharmaceutical applications and, in particular, in relation to body fluids, for example those of the gastrointestinal tract, that there may be local differences in the physiological conditions, especially the pH. If it is preferred, for example, for the active ingredient to be absorbed mainly in the duodenum, it may be advantageous for the binder component to be swellable under the conditions prevailing in the duodenum. In particular, it may be advantageous for only slight or preferably essentially no swelling to take place in the preceding sections of the gastrointestinal tract, especially in the stomach. However, it may be remarked at this point that such behavior of formulations of the invention after administration can also be ensured with other means, in the case described above for example with coatings resistant to gastric juice or multilayer formulations in which the innermost layers containing active ingredient are exposed to swelling or dissolving only at the required site.

In a particular embodiment, the binder component iii) forms no micelles under the conditions of use of the formulation. No CMC (critical micellar concentration) is reached.

Binder components technically advantageous for the process are those which are melt-processable.

It is preferred for at least one binder of the binder component to be selected from:

synthetic polymers such as polyvinyllactams, in particular polyvinylpyrrolidone (PVP); copolymers of vinyllactams such as N-vinylpyrrolidone, N-vinylpiperidone and N-vinyl-ε-caprolactam, but especially N-vinylpyrrolidone, with (meth)acrylic acid and/or (meth)acrylic esters, such as long-chain (meth)acrylates, e.g. stearyl (meth)acrylate, dialkylaminoalkyl (meth)acrylates, which may be quaternized, and maleic anhydride, vinyl esters, especially vinyl acetate, vinylformamide, vinylsulfonic acid or quaternized vinylimidazole; copolymers of vinyl acetate and crotonic acid; partially hydrolyzed polyvinyl acetate; polyvinyl alcohol; (meth)acrylic resins such as poly(hydroxyalkyl (meth)acrylates), poly(meth)acrylates, acrylate copolymers, e.g. from alkyl acrylates with (meth)acrylic acid, and copolymers of dimethylaminoethyl acrylates and methacrylic esters (e.g. Eudragit types); polyalkylene glycols such as polypropylene glycols and polyethylene glycols, preferably with molecular weights above 1 000, particularly preferably above 2 000 and very particularly preferably above 4 000 (e.g. polyethylene glycol 6 000); polyalkylene oxides such as polypropylene oxides and, in particular polyethylene oxides, preferably of high molecular weight, especially with weight average molecular weights of more than 100 000; copolymers of methyl methacrylate and acrylic acid; polyacrylamides, polyvinylformamide (where appropriate partially or completely hydrolyzed);

modified natural polymers, e.g. modified starches and modified celluloses, such as cellulose esters and, preferably cellulose ethers, e.g. methylcellulose and ethylcellulose, hydroxyalkyl-celluloses, in particular hydroxypropylcellulose, hydroxyalkyl-alkylcelluloses, in particular hydroxypropylmethylcellulose or hydroxypropylethylcellulose, cellulose phthalates, in particular cellulose acetate phthalate and hydroxypropylmethylcellulose phthalate, starch degradation products, in particular starch saccharification products, such as maltodextrin;

natural or predominantly natural polymers such as gelatin, polyhydroxyalkanoates, e.g. polyhydroxybutyric acid and polylactic acid, polyamino acids, e.g. polylysine, polyasparagine, polydioxanes and polypeptides, and mannans, especially galactomannans; and nonpolymeric binders such as polyols, for example those described in WO 98/22094 and EP 0 435 450, especially sugar alcohols such as maltitol, mannitol, sorbitol, cellobiitol, lactitol, xylitol, erythritol and isomalt (Palatinit).

In one embodiment of the present invention, at least one binder of the binder component is selected from the modified natural and, in particular, the synthetic polymers. In another embodiment of the present invention, at least one binder of the binder component is selected from the sugar alcohols or the starch saccharification products.

It is particularly preferred for at least one polymer of the binder component to be selected from polyvinylpyrrolidones, vinylpyrrolidone/vinyl acetate copolymers, hydroxyalkylcelluloses, hydroxyalkylalkylcelluloses, cellulose phthalates, polyalkylene glycols, (meth)acrylic resins: for example the polyvinylpyrrolidone having the proprietary name Kollidon® and weight average molecular weights of about 2 000 to about $1.5 \times 10^6$, for example the polyvinylpyrrolidone having the proprietary name Kollidon® 17 PF and a weight average molecular weight of about 7 000 to about 11 000; vinylpyrrolidone/vinyl acetate copolymers, in particular with a vinylpyrrolidone:vinyl acetate ratio of from about 30:70 to about 70:30, for example the product having the proprietary name Kollidon® VA 64 and a vinylpyrrolidone:vinyl acetate ratio of about 60:40; hydroxyalkylcelluloses with 1 to 3 carbon atoms in the alkyl moiety, in particular hydroxypropylcellulose, for example the hydroxypropylcellulose having the proprietary name Klucel®; hydroxyalkylalkylcelluloses with 1 to 3 carbon atoms in the alkyl moieties; in particular hydroxypropylmethylcellulose, for example the methylcellulose and methylcellulose derivative mixtures having the proprietary name Methocel® and containing ethyl, hydroxyethyl, hydroxypropyl and carboxymethyl ether groups, cellulose phthalates, especially hydroxypropylmethylcellulose phthalate, polyalkylene glycols with 2 and/or 3 carbon atoms in the alkylene moiety, especially polyethylene glycols, for example the polyethylene glycols having the proprietary name Lutrol® and weight average molecular weights of from 2 000 up to about 20 000, and polypropylene glycols, copolymers based on dimethylaminoethyl methacrylate and methacrylic esters such as methyl methacrylate and butyl methacrylate, for example the acrylic resins having the proprietary name Eudragit® E and based on dimethylaminoethyl methacrylate, methyl and butyl (meth)acrylate with weight average molecular weights of about 150 000, copolymers with anionic characteristics based on methacrylic acid and methyl methacrylate, for example the acrylic resins having the proprietary names Eudragit® L and S and with weight average molecular weights of about 250 000 and 135 000, respectively.

Very particular preference is given to the aforementioned polyvinylpyrrolidones and cellulose derivatives, especially Kollidon® VA 64 and low molecular weight hydroxypropylcellulose, e.g. Klucel® EF with weight average molecular weights of about 45 000 to about 70 000 or about 80 000, and hydroxypropylmethylcellulose, e.g. Methocel® E3, E5 and E7.

The binder component of formulations of the invention preferably comprises at least one of the binders described above. It may contain other binders of these types and/or other types. The properties of the formulation of the invention can be altered by nature of the binder chosen or the admixture of different binders. In particular, it is possible in this way to control the release of active ingredient.

In one embodiment of the present invention, the binder component consists of one of the binders described above. In another embodiment of the present invention, the binder component consists of a mixture of at least two of the binders described above.

In a specific embodiment of the present invention, the binder component comprises at least one sugar alcohol, which is preferably selected from maltitol, xylitol and isomalt, and/or one or more starch saccharification product(s), in particular maltodextrin, where appropriate in combination with one or more hydrophilic polymers, which are preferably selected from the abovementioned modified natural and synthetic polymers, e.g. polyvinylpyrrolidones, vinylpyrrolidone copolymers, especially with vinyl acetate, or cellulose derivatives, in particular hydroxypropylcelluloses, hydroxypropylmethylcelluloses or methylcelluloses, or polyethylene glycols. These constituents of this binder component are preferably present in the following ratios of amounts:

iii1) 5 to 90% by weight, preferably 10 to 50% by weight, and in particular 15 to 30% by weight, of at least one sugar alcohol and/or at least one starch saccharification product;

iii2) 10 to 95% by weight, preferably 50 to 90% by weight, and in partiulcar 70 to 85% by weight, of at least one hydrophilic polymer;

iii3) where appropriate, at least one of the polymers described above;

where the total of the contents of iii1), iii2), and iii3) comprises 100% by weight of the binder component.

Binders which are advantageous for use as polymeric binder are those which have a K value (according to H. Fikentscher, Cellulose-Chemie 13 (1932), pp. 58-64 and 71-74) in the range between 10 and 100, in particular between 15 and 80.

The content of the binder component in the formulation of the invention is usually 20 to 93.9% by weight, preferably 30 to 90% by weight and, in particular, 40 to 80% by weight.

In the pharmaceutical formulation sector, the content of the binder component in the formulation of the invention is, in particular, 20 to 80% by weight, preferably 30 to 60% by weight and, in particular, 40 to 50% by weight.

Formulations of the invention may, besides lipid component ii) or the lipid content of component i'), where appropriate in combination with component ii'), and binder component iii), contain further excipients, e.g. pharmaceutically and cosmetically acceptable excipients (excipient component iv). Such excipients may facilitate production of the formulation and/or modulate its properties. The nature and amount are advantageously chosen so that they do not impair development of the special properties of the formulations of the invention and of a molecular dispersion, in particular of a solid solution which is present where appropriate, or contribute to destabilizing this system.

Excipients are, for example, conventional pharmaceutical excipients, the total amount of which may be up to 100% by weight based on the binder component, for example, fillers such as the abovementioned sugar alcohols, e.g. mannitol, sorbitol, xylitol and isomalt (cf. DE 195 36 394), talc, sucrose, lactose, cereal or corn starch, potato flour, where present in particular in a concentration of 0.02 to 50, preferably 0.20 to 20, % by weight based on the total weight of the mixture;

lubricants, glidants and mold release agents such as magnesium, aluminum and calcium stearates, talc and silicones, and animal or vegetable fats, especially in hydrogenated form and those which are solid at room temperature. These fats preferably have a melting point of 30° C. or above. Technically preferred in relation to the melt extrusion process are—as described in DE 197 31 277—triglycerides of $C_{12}$, $C_{14}$, $C_{16}$ and $C_{18}$ fatty acids or—to improve the processing properties—lecithin, as described in connection with the extrusion of an isomalt-containing polymer/active ingredient melt in DE 195 36 394. It is also possible to use waxes such as carnauba wax. These fats and waxes may advantageously be admixed alone or together with mono- and/or diglycerides or phosphatides, in particular lecithin. The mono- and diglycerides are preferably derived from the abovementioned fatty acid types. The lipids which are present according to the invention normally carry out the function of these excipients, so that only small amounts and, advantageously, no lubricants, glidants and mold release agents are added as excipients to the formulation. Where present, the total amount of excipients in the form of lubricants and mold release agents is preferably 0.1 to 10% by weight and, in particular, 0.1 to 1% by weight, based on the total weight of the mixture;

flow regulators, e.g. diatomaceous earths, especially the high-purity silicon dioxides having the proprietary name Aerosil®, where present in particular in an amount of 0.1 to 5% by weight based on the total weight of the mixture;

dyes such as azo dyes, organic or inorganic pigments or dyes of natural origin, with preference being given to inorganic pigments where present in a concentration of 0.001 to 10, preferably 0.5 to 3% by weight based on the total weight of the mixture;

stabilizers such as antioxidants, light stabilizers, hydroperoxide destroyers, radical scavengers, stabilizers against microbial attack;

plasticizers, especially those described below.

It is also possible to add wetting agents, preservatives, disintegrants, adsorbents and mold release agents, and surfactants, especially anionic and nonionic, such as, for example, soaps and soap-like surfactants, alkyl sulfates and alkylsulfonates, salts of bile acids, alkoxylated fatty alcohols, alkoxylated alkylphenols, alkoxylated fatty acids and fatty acid glycerol esters, which may be alkoxylated, and solubilizers such as Cremophor (polyethoxylated castor oil), Gelucire, vitamin E TPGS and Tween (ethoxylated sorbitan fatty acid esters) (cf., for example, H. Sucker et al. Pharmazeutische Technologie, Thieme-Verlag, Stuttgart 1978). Since the formulations of the invention form emulsions on contact with water or aqueous solvents, it is possible to keep the addition of surface-active excipient, in particular substances with high HLB values, especially of more than 8, 10 and, in particular, above 15, low, usually in amounts of less than 1% by weight. It is possible and advantageous to dispense with such an addition.

Excipients for the purpose of the invention also mean substances for producing a solid solution with the active ingredient. Examples of these excipients are pentaerythritol and pentaerythritol tetraacetate, urea, phosphatides such as lecithin, and sugar alcohols such as xylitol and mannitol, citric and succinic acids, bile acids, stearins and others as indicated, for example, by J. L. Ford, Pharm. Acta Helv. 61, (1986), pp. 69-88.

Also regarded as excipients are additions of acids and bases to control the solubility of an active ingredient (see, for example, K. Thoma et al., Pharm. Ind. 51, (1989), pp. 98-101).

It is also possible to add excipients such as masking flavors and odor-masking agents, in particular sweeteners and odorants.

An embodiment of this type is based on expert knowledge as described, for example, in Fiedler, H. B., Lexikon der Hilfsstoffe für Pharmazie, Kosmetik, und angrenzende Gebiete, 4th edition, Aulendorf: ECV-Editio-Cantor-Verlag (1996).

Excipients in the sense of the invention are also vehicles specific for the dosage form, i.e. appropriate for a particular dosage form, in particular oral and, especially, tablets and capsules, also low-melting or liquid excipients such as polyalkylene glycols of low molecular weight, in particular polyethylene glycol and/or polypropylene glycol with weight average molecular weights of less than 1 000, water or suitable aqueous systems.

The excipient component in formulations of the invention preferably comprises at least one of the other excipients described above. It may comprise other excipients of these types and/or other types.

One embodiment of the present invention comprises formulation bases with excipient component. In this case, the content of other excipients in the formulations of the invention can be up to 30% by weight, preferably 1 to 20% by weight and, in particular, 6 to 15% by weight.

A particular embodiment of the present invention comprises formulations which comprise
  i) at least one active ingredient, preferably an active pharmaceutical ingredient;
  ii) at least one unsaturated fatty acid, which is preferably selected from oleic acid, linoleic acid and/or linolenic acid, or corresponding mono- or diglycerides;
  iii) at least one binder which is selected from polyvinylpyrrolidones, vinylpyrrolidone copolymers, in particular with vinyl acetate, or cellulose derivatives, in particular hydroxypropylcelluloses and hydroxypropyl-methyl-celluloses; and
  iv) where appropriate other excipients, for example a flow regulator.

Another particular embodiment of the present invention comprises formulations which comprise
  i') at least one lipid-like active ingredient, preferably an oil and, in particular, an essential oil;
  ii') where appropriate one or more other lipids;
  iii) at least one sugar alcohol, in particular maltitol and/or isomalt, and at least one starch saccharification product, in particular maltodextrin; and
  iv) where appropriate other excipients.

Formulations of this type may, in particular, also comprise other binders such as the abovementioned modified natural and synthetic polymers, e.g. polyvinylpyrrolidones, vinylpyrrolidone copolymers, in particular with vinyl acetate, or cellulose derivatives, in particular hydroxypropylcelluloses, hydroxypropylmethylcelluloses or methylcellulose, or polyethylene glycols.

The formulations of the invention preferably contain less than 5% by weight and, in particular, less than 1% by weight of water. A particular embodiment is represented by essentially anhydrous formulations.

The formulations of the invention preferably have a solid consistency. The term "solid" has in this connection the meaning assigned in appropriate pharmacopeas in connection with pharmaceutical preparations. Formulations of the invention may also be of semisolid or viscous liquid consistency. The terms "semisolid" and "viscous liquid" also have within the framework of the present invention the meanings assigned in appropriate pharmacopeas in connection with pharmaceutical preparations. For example, formulations of the invention may be of semisolid consistency if the contents of lipids and, in particular low-melting lipids are relatively high. A semisolid and, if desired, also viscous liquid consistency can, as is well known, also be achieved by adding suitable excipients, in particular low-melting or liquid vehicles.

The present invention therefore also relates to the use of a formulation of the invention where appropriate with the addition of other excipients as dosage form for the use of at least one active ingredient in the life science sector.

Accordingly, formulations of the invention are mainly used in the life science sector. This includes, in particular, the pharmaceutical, both human and veterinary medical, sector. In this sense, the formulations are used as or in drug forms, i.e. the formulations of the invention have expedient forms appropriate for pharmaceutical practice, if necessary together with other excipients. Analogous statements apply to the cosmetic sector and adjoining areas such as crop protection, the foodstuffs sector and the like. Reference is made here inclusively to a use as or in dosage forms, where the term "dosage form" means a formulation shaped with a view to the use.

Thus, the term "drug form" refers to any dosage form for administration of active ingredients to an organism, preferably to mammals, in particular humans, and also an agricultural or domestic animals.

Conventional dosage forms include, in particular, drug forms such as (in alphabetical sequence) emulsions and microemulsions, granules, capsules, pellets, powders, suspensions, suppositories, tablets, especially coated tabl ts, and analogous dosage forms for use in other life sci nc sectors.

Emulsions and microemulsions may be of the oil-in-water or water-in-oil type and contain the formulations of the invention as disperse or dispersing phase. These emulsions or microemulsions may be stabilized by the presence of emulsifiers known to be used for this purpose. One advantage of formulations of the invention is, however, usually only small amounts of emulsifier are added and, in a particular embodiment of the present invention, it is possible to dispense with addition of emulsifiers, in particular O/W emulsifiers with HLB values over 10 and, in particular, over 15.

Granules consist of solid grains of formulations of the invention, each grain representing an agglomerate of powder particles. Granules are preferably intended for oral use as drug form. The user can be offered single-dose preparations, for example granules packed in a small bag (sachet), a paper bag or a small bottle, or multidose preparations which require appropriate dimensions. However, in many cases, such granules do not represent the actual drug form, but are intermediates in the manufacture of particular drug forms, for example tablet granules to be compressed to tablets, capsule granules to be packed into hard gelatin capsules, or instant granules or granules for oral suspension to be put in water before intake.

As capsules, the formulations of the invention are usually packed into a hard shell composed of two pieces fitted together or a soft, one-piece, closed shell, which may vary in shape and size. It is likewise possible for formulations of the invention to be encased or enveloped or embedded in a matrix in suitable polymers, that is to say microcapsules and microspherules. Hard and soft capsules consist mainly of gelatin, while the latter have a suitable content of plasticizing substances such as glycerol or sorbitol. Hard gelatin capsules are used to receive formulations of the invention which have a solid consistency, for example granules, powder or pellets. Soft gelatin capsules are particularly suitable for formulations with a semisolid consistency and, if required, also viscous liquid consistency.

Pellets are granules of formulations of the invention in the particle size range from about 0.5 to 2 mm in diameter. Both with a narrow particle size distribution, preferably from 0.8 to 1.2 mm, and with an essentially round shape, are preferred.

In semisolid preparations, formulations of the invention are taken up in a suitable vehicle. Appropriate bases are known to the pharmaceutical technologist.

Suppositories are solid preparations for rectal, vaginal or urethral administration. In order to be appropriate for the administration route, formulations of the invention in these drug forms are usually taken up in suitable vehicles, for example in fats which melt at body temperature, such as hard fat, macrogols, i.e. polyethylene glycols with molecular weights of 1 000 to 3 000 in various proportions, glycerol gelatin and the like.

Tablets are solid preparations in particular for oral use. The meaning of oral within the framework of the present invention is, in particular, that of the term "peroral", i.e. tablets for absorption or action of the active ingredient in the gastrointestinal tract. Particular embodiments are coated tablets, layered tablets, laminated tablets, tablets with modified release of active ingredient, matrix tablets, effervescent tablets, chewable tablets or pills. The formulations of the invention usually comprise at least a part of the necessary tablet excipients, such as binders, fillers, glidants and lubricants, and disintegrants. Tablets of formulations of the invention may also if necessary comprise other suitable excipients. Mention should be made in this connection of excipients which assist tableting, for example lubricants and glidants, for example those mentioned above, with preference for magensium stearate in particular for facilitating compaction.

Coated tablets additionally comprise suitable coating materials, for example film coating agents with coating aids, especially those mentioned below. Coated tablets include, in particular, sugar-coated tablets and film-coated tablets.

Powders are finely dispersed solids of formulations of the invention with particle sizes usually of less than 1 mm. The above statements about granules apply correspondingly.

Preference is given according to the invention to capsules packed with comminuted granules, powders or pellets of formulations of the invention, instant granules and granules for oral suspension composed of formulations of the invention with addition of masking flavors, and, in particular, tablets.

The drug forms of the invention are usually packed in a suitable form. Pushout packs made of plastic and/or metal for solid drug forms are frequently used.

The present invention also relates to a process for producing a formulation of the invention by mixing components i), ii), iii) and, where appropriate, iv) to form a plastic mixture. Thus, to form the plastic mixture, at least two measures are necessary, on the one hand the mixing of the components forming the mixture, and on the other hand the plastication thereof, i.e. the conversion thereof into the plastic state. These measures may take place for one or more components or portions of components successively, intermeshingly, alternately or in another way. Accordingly, it is possible in principle for the conversion into the plastic state to take place concurrently during a mixing process, or for the mixture first to be mixed and then to be converted into the plastic state. A plurality of plastic mixtures differing in composition may be formed during a process and are mixed together and/or with other components or portions of components. For example, a premix of a portion of the components can be granulated to form a plastic mixture, and the granules can then be converted, with the addition of other components, into another plastic mixture whose composition may correspond to that of the formulation. It is also possible for all the components first to be combined and then either converted into the plastic state at the same time of the mixing or first mixed and then converted into the plastic state.

The formation of a plastic mixture can take place by melting or—with additional input of mechanical energy, e.g. by kneading, mixing or homogenizing—melts below the melting point of the mixture. The plastic mixture is preferably formed at temperatures below 220° C. The formation of the plastic mixture usually does not take place by one or more components being converted into a paste or partially dissolved with liquids or solvents, but takes place mainly or exclusively by thermal or thermal/mechanical action on the component(s), i.e. by thermal plastication. The plastic mixture is preferably formed by extrusion, particularly preferably by melt extrusion. The plastication process steps can be carried out in a manner known per se, for example as described in EP-A-0 240 904, EP-A-0 337 256, EP-A-0358 108, WO 97/15290 and WO 97/15291. The contents of these publications and, in particular, the statements about melt extrusion present therein are incorporated herein by reference.

It should be possible to convert the binder component into a plastic state in the complete mixture of all the components in the range from 30 to 200°C., preferably 40 to 170° C. The glass transition temperature of the mixture should therefore be below 220° C., preferably below 180° C. If necessary, it is reduced by conventional, pharmacologically acceptable plasticizing excipients.

Examples of such plasticizers are:
organic, preferably involatile compounds, such as, for example, $C_7$-$C_{30}$-alkanols, ethylene glycol, propylene glycol, glycerol, trimethylolpropane, triethylene glycol, butandiols, pentanols such as pentaerythritol and hexanols, polyalkylene glycols, preferably having a molecular weight of from 200 to 1 000, such as, for example, polyethylene glycols, polypropylene glycols and polyethylene/propylene glycols, silicones, aromatic carboxylic esters (e.g. dialkyl phthalates, trimellitic esters, benzoic esters, terephthalic esters) or aliphatic dicarboxylic esters (e.g. dialkyl adipates, sebacic esters, azelaic esters, citric and tartaric esters), fatty acid esters such as glycerol mono-, di- or triacetate or sodium diethyl sulfosuccinate. The concentration of plasticizer is, where present, generally 0.5 to 30, preferably 0.5 to 10, % by weight based on the total weight of polymer and plasticizer.

The amount of plasticizer advantageously does not exceed 30% by weight based on the total weight of binder and plasticizer so that—in the area of solid forms—storage-stable formulations and drug forms showing no cold flow are formed. It is usually unnecessary to add a plasticizer for the purpose of plastication because the lipid component present according to the invention has plasticizing properties.

The process of the invention can advantageously be carried out at temperatures below 200° C. and preferably below 170° C., but above room temperature (25° C.), preferably above 40° C. The process is carried out in particular in a temperature range extending 40° C., preferably 30° C., and particularly preferably 20° C., upward or downward from the softening point of the mixture of the components.

In certain cases it may be advantageous to add components or portions of components as solution or suspension in a solvent. Particularly expedient ones are low molecular weight volatile solvents, e.g. water, $C_1$-$C_6$-monoalcohols and ethers thereof, esters of $C_1$-$C_6$-monoalkanols with $C_1$-$C_6$-carboxylic acids, alkanes. Another solvent which can be used is liquid $CO_2$. Water-soluble active ingredients can be employed as aqueous solution or, preferably, be taken up in an aqueous solution or dispersion of the binder component or a portion thereof. Corresponding statements apply to active ingredients which are soluble in one of the solvents mentioned, if the liquid form of the components used is based on an organic solvent. The components to be employed according to the invention may contain small amounts of solvent, e.g. because of hygroscopicity, trapped solvent or water of crystallization. The total solvent content of the plastic mixture is preferably less than 15%, in particular less than 10%, and particularly preferably less than 5%. The plastic mixture is preferably formed without the addition of a solvent, i.e. in particular by solvent-free melt extrusion.

The components, i.e. active ingredient, lipid and binder and, where appropriate, other excipients, can first be mixed and then be converted into the plastic state and homogenized. However, it has proved advantageous, especially on use of sensitive active ingredients, first to convert at least part of the binder component and at least part of the lipid component, where appropriate together with other excipients, into the plastic state. This can be done by operating the apparatuses such as stirred vessels, agitators, solids mixers etc. alternately. Sensitive active ingredients can then be mixed in (homogenized), preferably in "intensive mixers" in plastic phase with very small residence times. The active ingredient(s) may be employed as such, i.e. in solid, semisolid or liquid form, or as solution, suspension or dispersion.

In particular embodiments of the process of the invention, it may be advantageous initially to form a plastic mixture of binder and active ingredient and, where appropriate, excipients and to add the lipid to this mixture. This procedure may be advantageous in particular when the active ingredient has plasticizer-like properties, and the reduction in the overall process temperature achievable thereby is desirable.

In particular embodiments of the process of the invention it may be advantageous for the active ingredient and lipid first to be mixed and then to be added to the plasticated binder. This procedure may be advantageous in particular when active ingredient and/or lipid are thermally unstabl The plastication, melting and/or mixing takes place in an apparatus usual for this purpose. Extruders or heatable containers with agitator, e.g. kneaders (like those of the type mentioned hereinafter) are particularly suitable.

It is also possible to use as mixing apparatus those apparatuses which are employed for mixing in plastics technology. Suitable apparatuses are described, for example, in "Mischen beim Herstellen und Verarbeiten von Kunststoffen", H. Pahl, VDI-Verlag, 1986. Particularly suitable mixing apparatuses are extruders and dynamic and static mixers, and stirred vessels, single-shaft stirrers with stripper mechanisms, especially paste mixers, multishaft stirrers, especially PDSM mixers, solids mixers and, preferably mixer/kneader reactors (e.g. ORP, CRP, AP, DTB from List or Reactotherm from Krauss-Maffei or Ko-Kneader from Buss), trough mixers or internal mixers or rotor/stator systems (e.g. Dispax from IKA).

In the case of sensitive active ingredients it is preferable first for the binder component and the lipid component to be converted into the plastic state, e.g. in an extruder, and then for the active ingredient to be admixed in a mixer/kneader reactor. On the other hand, with less sensitive active ingredients, a rotor/stator system can be employed for vigorously dispersing the active ingredient.

The process steps of mixing and plastication, that is to say in particular the melting, can be carried out in the same apparatus or in two or more apparatuses operating separately from one another. The preparation of a premix can be carried out in one of the mixing apparatuses described above and normally used in particular for granulation. Such a premix can then be fed directly for example into an extruder, and then be extruded where appropriate with the addition of other components.

It is possible in the process of the invention to employ as extruders single screw machines, intermeshing screw machines or else multiscrew extruders, especially twin screw extruders, corotating or counter-rotating and, where appropriate, equipped with kneading disks. If it is necessary in the extrusion to evaporate a solvent, the extruders are generally equipped with an evaporating section. Examples of extruders which can be used are those of the ZSK series from Werner & Pfleiderer.

The mixing apparatus is charged continuously or batchwise, depending on its design, in a conventional way. Powdered components can be introduced in a free feed, e.g. via a weigh feeder. Plastic compositions can be fed in directly from an extruder or via a gear pump, which is particularly advantageous if the viscosities and pressures are high. Liquid media can be metered in by a suitable pump unit.

The lipid component can—as described above—be incorporated continuously or batchwise into the formulation. Thus, at least part of the binder component (matrix) can first be used as support for at least part of the lipid component, and then be formulated according to the invention as premix to form a plastic mixture, possibly with addition of other ingredients, preferably by extrusion. Continuous addition of at least part of the lipid component to a plastic mixture is preferred. This is particularly preferred when the lipids to be used according to the invention can be processed in semisolid or liquid form. Accordingly, the lipids described above and having relatively low melting points are also preferred for technical reasons in the process, and of these in turn preference is given to those which at room temperature, i.e. about 20 to 30° C., are of semisolid (waxy), and preferably of liquid (oil) consistency. It is preferred for these to be metered directly into the mixing apparatus, in particular an extruder. This may save a granulation step to be carried out separately. It is particularly advantageous to incorporate the lipid-like active ingredients, that is to say in particular the essential oils, continuously into the appropriate binder matrix, preferably in an extruder, feeding the oil continuously into an extruder carrying the binder mixture, and extruding the resulting formulation as plastic mixture.

The mixture which has been obtained by mixing and converting the binder component, the active ingredient component, the lipid component and, where appropriate, other excipients into the plastic state is pasty, of high viscosity or low viscosity (thermoplastic) and can therefore also be extruded. The glass transition temperature of the mixture is advantageously below the decomposition temperature of all the components present in the mixture.

The formulation of the invention is suitable as plastic mixture—where appropriate after cooling or solidification—in particular as extrudate, for all conventional processes for manufacturing conventional dosage forms.

The present invention also relates to a process for producing dosage forms of formulations of the invention, where the formulation can be produced by the above process, and the formulation is converted into the required dosage form where appropriate with the addition of other excipients. This can be done by using shaping process measures such as shaping the plastic mixture, in particular by extrusion or melt extrusion, and shaping the plastic mixture, in particular the extrudate—where appropriate after cooling or solidification—for example by granulation, grinding, compression, casting, injection molding, tableting under pressure, tableting under pressure with heat. It is also possible to convert a formulation into a desired dosage form by introducing it into suitable vehicles. It is thus also possible to process solid formulations into semisolid or liquid formulations through the addition of suitable vehicles.

A large number of, in particular, solid dosage forms can be manufactured in this way. For example, powders or granules can be produced by grinding or chopping the solidified or at least partly solidified plastic mixture, and can be either used directly or, where appropriate with addition of conventional excipients, further processed to the above dosage forms, especially to tablets.

Dosage forms are preferably shaped before solidification of the plastic mixture and result in a form which can be employed where appropriate after coating in a conventional way.

The shaping to the dosage form before solidification can take place in a variety of ways depending on the viscosity of the plastic mixture, for example by casting, injection molding, compression, nipping or calendering. This is done by conveying the plastic mixture described above in the process according to the invention to one or more shaping steps. The conveying can take place by pressing, pumping, e.g. with gear pumps, or, preferably, with an extruder.

The plastic mixture is particularly preferably formed in one or more, preferably one, extruder and conveyed by the latter or a downstream extruder to the shaping steps. It has proved to be advantageous in many cases to extrude on a downward incline and/or where appropriate provide a guide channel for transporting the extrudate, in order to ensure safe transport and prevent rupture of the extrudate.

It may also be advantageous, depending on the number and compatibility of the active ingredients to be employed, to employ multilayer extrudates, for example coextrudates, as described in WO 96/19963, in the process of the invention.

Multilayer solid dosage and, in particular, drug forms can be produced in particular by coextrusion, in which case a plurality of mixtures of one or more of the components described above are conveyed together into an extrusion die so that the required layer structure results. Different binders are preferably used for different layers.

Multilayer dosage and, in particular, drug forms preferably comprise two or three layers. They may be in open or closed form, in particular as open or closed multilayer tablets.

If the shaping takes place by coextrusion, the mixtures from the individual extruders or other units are fed into a common coextrusion die and extruded. The shape of the coextrusion dies depends on the required drug form. Examples of suitable dies are those with a flat orifice, called slit dies, and dies with an annular orifice. The design of the die depends on the formulation base used and, in particular, the binder component and the desired shape.

The first shaping step advantageously takes place when the extrudate emerges from the extruder through suitably shaped dies, draw plates or other orifices, for example through a baker plate, a circular die or a slit die. This usually results in a continuous extrudate, preferably with a constant cross section, for example in the form of a ribbon or of a strand, preferably with a circular, oval, rounded or flat and broad cross section.

Suitable downstream shaping steps for extrudates are, for example, cold cut, that is to say the cutting or chopping of the extrudate after at least partial solidification, hot cut, that is to say the cutting or chopping of the extrudate while still in the plastic form, or pinching off the still plastic extrudate in a nip device. It is possible with hot or cold cut to obtain, for example, granules (hot or cold granulation) or pellets. Hot granulation usually leads to dosage forms (pellets) with a diameter of from 0.5 to 3 mm, while cold granulation normally leads to cylindrical products with a length to diameter ratio of from 1 to 10 and a diameter of from 0.5 to 10 mm. It is possible in this way to produce monolayer but also, on use of coextrusion, open or closed multilayer dosage forms, for example oblong tablets, pastilles and pellets. The dosage forms can be provided with a coating by conventional methods in a downstream process step. Suitable materials for film coatings are the polymers mentioned as polymeric binders, in particular polyacrylates such as the Eudragit® types, cellulose esters such as the hydroxypropylcellulose phthalates, and cellulose ethers such as ethylcellulose, hydroxypropylmethylcellulose or hydroxypropylcellulose, and gelatin. Further shaping steps may also follow, such as, for example, rounding off the pellets obtained by hot or cold cut using rounding-off devices as described in DE-A-196 29 753.

It is particularly preferred for all the shaping steps to be carried out on the still plastic mixture or still plastic extrudate. Besides hot cut, where appropriate with subsequent rounding off, a particularly suitable process is one in which the plastic mixture is shaped to the dosage form in a molding calender. This is done by conveying a still plastic mixture or a still plastic extrudate to a suitable molding calender. Suitable molding calenders usually having molding rolls and/or belts for the shaping, with at least one of the molding rolls and/or at least one of the belts having depressions to receive and shape the plastic mixture. It is preferred to use a molding calender with counter-rotating molding rolls, with at least one of the molding rolls having on its surface depressions to receive and shape the plastic mixture. Suitable molding calenders and devices containing molding rolls are generally disclosed for example in EP-A-0 240 904, EP-A-0 240 906 and WO 96/19962, and suitable belts and devices containing belts are generally disclosed for example in EP-A-0 358 105, which are expressly incorporated herein by reference.

The shaping of the still plastic mixture or still plastic extrudate preferably takes place at temperatures below 220° C., particularly preferably below 180° C. and very particularly preferably below 150° C., such as, for example, in the temperature ranges necessary to form the plastic mixture or at lower temperatures. If the shaping takes place at lower temperatures, it advantageously takes place at from 5 to 70° C., preferably 10 to 50° C. and particularly preferably 15 to 40° C. below the highest temperature reached on formation of the plastic mixture, but preferably above the solidification temperature of the plastic mixture.

The production according to the invention of the formulations and preparation of the dosage forms can be carried out wholly or partly under sterile operating conditions, for example in cleanrooms and with use of sterilized equipment such as, for example, weighers, mixers, extruders and shaping machines, such as calenders, nip devices and choppers. It is possible either for the starting materials to be introduced into the process in sterilized form, where appropriate with the addition of suitable antibacterial and/or antiviral excipients, and/or for the process conditions, especially the temperature, to be chosen such that sterile formulations or drug forms are obtained. The resulting sterile dosage forms can then be packaged directly, likewise under sterile conditions, for example by blister packing or sealing. The shaping and the packaging may also be carried out at the same time, in particular when the shaping of the plastic mixture by calendering is carried out by molding rolls. This is done by introducing, in addition to the plastic mixture, materials in the form of sheets between the melt and the molding roll in each case, whereby it is possible to achieve at the same time as the shaping of the plastic mixture to dosage forms an enveloping and/or a packaging of the dosage form, as described in WO-96/19963, which is incorporated herein by reference.

The present invention further relates to the use of a formulation base of the invention in the use of at least one active ingredient in the life science sector, that is to say, in particular, in the drugs, cosmetics, crop protection, foodstuffs, and washing, cleaning and hygiene sectors.

The purpose of this use is, in particular, to improve the effect of the active ingredient component. Thus, this use comprises in particular a process for improving the effect of the active ingredient component on use of at least one active ingredient in the life science sector, with use of a formulation base of the invention. This entails introducing at least one active ingredient into this formulation base, preferably using one of the processes described above. In particular, the binder matrix of the formulation base serves to receive at least one lipid in the production of a solid formulation of the invention to improve the effect of the active ingredient component.

The binder matrix is formed by the binder component described above or at least a part thereof. At least one lipid, which is a constituent of the lipid component described above and/or of the active ingredient component, is taken up in this binder matrix. It is particularly preferred for the taking up to result in an essentially molecular dispersion of lipid in the binder matrix. A homogeneous distribution of lipid in the matrix is advantageous, especially in relation to the active ingredient-promoting properties of the lipid. These advantages can be achieved even without the active ingredient being in a molecular dispersion. Lipids which can be used to improve the pharmacological effect of an active ingredient are known to the skilled worker, inter alia as absorption promoters. He is able to select at least part of the lipid component for example from among them. In addition, reference is made to the statements above in connection with the description of the lipid component.

The use according to the invention is particularly advantageous whenever active ingredients are to be used in such a way that an active ingredient-promoting effect may occur on simultaneous administration of lipids. This relates in the pharmacy sector in particular to routes of administration which include the gastrointestinal tract, that is to say, in particular, enteral, especially rectal and, preferably, oral administration. The use according to the invention is very particularly advantageous when an active pharmaceutical ingredient to be administered can be used only inadequately by this route without suitable measures such as the addition of at least one lipid.

The invention also relates to the use of a formulation of the invention where appropriate with the addition of other excipients as dosage form in the life science sector.

The dosage forms include, in particular, the aforementioned drug forms. Corresponding dosage forms for cosmetic use, for plant treatment, for food technology, including human and animal food technology, and other adjoining areas can be manufactured taking account of expedient, use-specific embodiments. The use according to the invention is directed in particular at human and veterinary medical treatment, cosmetic treatment, crop protection, the supplementation of human and animal foods with active ingredients, and the inclusion of active ingredients in washing, cleaning and hygiene products.

A particular use relates to the addition of formulations of the invention to hygiene products, especially diapers for babies. The formulations particularly used within the framework of this use are those based on lipid-like active ingredients. It is thus possible to use solid or semisolid formulations with odorants or other hydrophobic active ingredients, e.g. substances with antimicrobial activity, especially the aforementioned essential oils. When these formulations come into contact with body fluids they form an emulsion whose large surface area allows odorants in particular to act efficiently.

Drug forms of the invention, and thus an effective amount of active ingredient, are administered to the individual to be treated, preferably a mammal, in particular a human, and also an agricultural or domestic animal. Whether such a treatment is indicated and what form it is to take depends on the individual case and is subject to medical assessment (diagnosis) which includes the signs, symptoms and/or dysfunctions which are present, the risks of developing certain signs, symptoms and/or dysfunctions, and other factors. The drug forms of the invention are usually administered one or more times a day together or alternately with other products in such a way that an individual to be treated receives a daily dose in an amount which makes therapy possible.

The formulations of the invention represent self-emulsifying systems. Emulsions are formed when the formulations come into contact with aqueous media. Accordingly, the present invention also relates to a process for producing emulsions. These emulsions are usually stable, especially under the conditions of use of the formulations of the invention. Thus, the formulations usually form stable emulsions even at temperatures below 90° C. Preferred temperature ranges for the formation of stable emulsions are from 5 to 60° C. and, in particular from 10 to 40° C. It is advantageous for these to be fine-particle emulsions with a predominant content of particles with diameters of less than 100 µm, preferably of less than 50 µm and, in particular, of less than 20 µm. Formulations which form emulsions on contact with aqueous medium and in which at least 50% of the particle diameters are in a range from 100 to 20 000 nm, preferably from 10 to 5 000 nm and, in particular, from 300 to 2 000 nm are preferred embodiments.

Under the conditions of use, the emulsions normally form spontaneously. In particular, negligible input of mechanical energy, e.g. stirring and/or shear energy, is necessary. Thus, formulations of the invention can initially be produced in the absence of solvents. The formation of the emulsion then takes place, depending on the use, when contact is made with an aqueous medium, in the drug form sector before administration by preparing an appropriate dosage form or after administration on contact with a suitable body fluid.

The formation of fine-particle emulsions is assisted especially through the formulations of the invention being in the state of a molecular dispersion and in particular a solid solution.

Thus, formulation bases of the invention are particularly preferred when lipid emulsions are preferred for the use of active ingredients. This particularly relates to active ingredients of low solubility; active ingredients which, although readily soluble, display an only inadequate effect on enteral administration; and/or active ingredients which cause local irritation and/or other unwanted side effects. This applies just as much to topical administration forms such as, for example, lotions, creams and ointments as to parenteral administration forms such as, for example, solutions for injection, and oral administration forms, e.g. drinkable solutions and solid dosage forms, for example tablets and capsules.

The use of the aforementioned binders in particular has its effect in the formation of the emulsions. These binders and, in particular, the polymeric binders are able to act as solubilizers and thus assume the function of emulsifiers as in relation to the emulsification of the lipids. A further aspect of the present invention is therefore the use of the binder component for emulsifying the lipid component.

The present invention is now to be illustrated, but not restricted, by means of the following examples.

EXAMPLE 1

A mixture of equal parts by weight of hydroxypropylcellulose (Klucel EF, Aqualon) and oleic acid was processed at 120° C. in a measuring kneader (Rheomix, from Haake) to a homogeneous, rubber-like melt. Cooling resulted in a transparent solid mass which dissolved in water to form an emulsion.

EXAMPLE 2

The experiment took place in analogy to example 1, but with a mixture of 60% by weight of Kollidon VA-64 (BASF) and 40% by weight of oleic acid at a temperature of 100° C. over 5 minutes. A clear, low-viscosity, transparent melt was obtained and was, after cooling to room temperature (and even after storage at room temperature for 12 months), clearly transparent and still plastically deformable. The cooled melt dissolved readily to form an emulsion in water. The size of the emulsion droplets in this preparation was measured using a Mastersizer instrument (from Malvern, UK). 90% of the particles had sizes below 35 μm, and 50% of the particles were smaller than 2 μm.

EXAMPLE 3

The experiment took place in analogy to example 2, with a mixture of 72% by weight of Kollidon VA-64 (BASF) and 28% by weight of oleic acid. The cooled melt was likewise transparent but less readily plastically deformable than in Example 2. The cooled melt dissolved readily in water to form an emulsion. The size of the emulsion droplets in this preparation was measured using a Mastersizer instrument (from Malvern, UK). 90% of the particles had sizes below 4 μm, and 50% of the particles were smaller than 0.7 μm.

EXAMPLE 4

The experiment took place as in example 3, but with a mixture of 64% by weight of Kollidon VA-64 (BASF), 16% by weight of oleic acid and 20% by weight of dextran at 118° C. The resulting whiteish melt became solid after cooling and it dissolved quite rapidly in 0.1 M HCl to form an emulsion.

EXAMPLE 5

The experiment took place as in example 4, but with a mixture consisting of 70% by weight of hydroxypropylcellulose (Klucel EF, Aqualon), 10% by weight of oleic acid and 20% by weight of dextran at 120° C. The resulting white melt became solid after cooling and dissolved in water to form an emulsion, but more slowly than in the case of example 4.

EXAMPLE 6

The experiment took place as in example 5, but with a mixture consisting of 40% by weight of hydroxypropylcellulose (Klucel EF, Aqualon), 40% by weight of stearic acid and 20% by weight of dextran at 120° C. The resulting white melt was, after cooling and grinding, relatively easily dispersible in water to form an emulsion.

EXAMPLE 7

The experiment took place as in example 1, but with a mixture consisting of 70% by weight of hydroxypropylcellulose (Klucel EF, Aqualon) and 30% by weight of stearic acid at 110° C. A clear, rubber-like melt formed and, on cooling, formed a white solid.

EXAMPLE 8

1 part by weight of oleic acid was added to 7 parts by weight of Kollidon VA-64 (BASF) with gentle kneading. Kneading for a few minutes resulted, with slight evolution of heat, in homogeneous granules which were mixed with 2 parts by weight of the active ingredient esuprone. 1% by weight of highly disperse silica (Aerosil 200) was then added to this granular mixture, and this mixture was then metered via a weigh feeder into a twin screw extruder (16 mm screw diameter) and extruded at a temperature of 110° C. The resulting clear melt could, after cooling, be dissolved in water to form an emulsion.

EXAMPLE 9

The experiment was carried out in analogy to example 8 but with 2 parts by weight of paracetamol which had been kneaded with a previously granulated mixture of 7 parts by weight of Kollidon VA-64 (BASF) and 1 part by weight of oleic acid. 1% by weight of Aerosil 200 was likewise added to the overall mixture while mixing before the extrusion. The extrusion took place at a temperature of 125° C., and the cooled melt dissolved in water to form a fine-particle emulsion.

EXAMPLE 10

The experiment took place as in example 8 but with with 2 parts by weight of paracetamol and a granular mixture of 6.125 parts by weight of Kollidon VA-64 (BASF), 0.875 parts by weight of oleic acid and 1 part by weight of stearyl alcohol. 1% by weight of Aerosil 200 was likewise added to the overall mixture while mixing before the extrusion. The extrusion took place at a temperature of 120° C., and the cooled melt dissolved in water to form a fine-particle emulsion.

Examples 11 to 13 which follow illustrate formulations of the invention with lipid-like active ingredients, in these cases orange oil as essential oil. The mixtures were processed in a Werner & Pfleiderer ZSK30 twin screw extruder with a throughput of 2.7 kg/hour. The shaping of the still plastic extrudate took place as described in EP-A 240 906. The metering in from the side took place with an HPLC pump with a pumping rate of 300 g/h in section 2.

EXAMPLE 11

2% by weight of a PVP homopolymer with a K value of 30 (Kollidon 30), 70% by weight of isomalt, 18% by weight of maltodextrin with DE 15 (C-Pur 01915, from Cerestar) were mixed in a twin screw extruder. 10% by weight of orange oil were metered in from the side and continuously incorporated into the matrix. After extrusion, the mixture was converted into pellets about 1 mm in size by hot cut. The temperature in the individual sections was 39° C., 57° C., 110° C., 89° C. and 89° C., and that of the die was 101° C.

EXAMPLE 12

2% by weight of hydroxypropylcellulose with a weight average molecular weight of about 80 000 (Klucel EF), 70% by weight of isomalt, 18% by weight of maltodextrin with DE 15 (C-Pur 01915, from Cerestar) were mixed in a twin screw extruder. 10% by weight of orange oil were metered in from the side and continuously incorporated into the matrix. After extrusion, the mixture was converted into pellets about 1 mm in size by hot cut. The temperature in the sections was 61° C., 84° C., 120° C., 111° C. and 100° C., and that of the die was 111° C.

EXAMPLE 13

2% by weight of a PVP homopolymer with a K value of 30 (Kollidon 30), 53% by weight of isomalt, 35% by weight of maltodextrin with DE 15 (C-Pur 01915, from Cerestar) were mixed in a twin screw extruder. 10% by weight of orange oil were metered in from the side and continuously incorporated into the matrix. After extrusion, the mixture was converted into pellets about 1 mm in size by hot cut. The temperature in the sections was 52° C., 64° C., 110° C., 92° C. and 91° C., and that of the die was 104° C.

We claim:
1. A solid, self-emulsifying formulation comprising
i) an active pharmaceutical ingredient
ii) 6 to 60% by weight of a lipid component, wherein the lipid component has an HLB of not exceeding 12 and has a melting point of not exceeding 40 ° C.; and
iii) 20 to 93.9% by weight of a binder component comprising a binder selected from polyvinylpyrrolidones, vinylpyrrolidone/vinylacetate copolymers, hydroxyalkylcelluloses, hydroxyalkylalkylcelluloses, cellulose phthalates or (meth)acrylic resins;
wherein the content of the lipid component based on the binder component does not exceed 40% by weight, and wherein the formulation is essentially free of lipid and active pharmaeutical ingredient crystals, and the formulation comprises a molecular dispersion of the lipid component in the binder component.

2. The formulation of claim 1, wherein the active pharmaceutical ingredient has a low solubility in water.

3. The formulation of claim 1, wherein the lipid component has a melting point of less than 30°C.

4. The formulation of claim 1, wherein the lipid component is in the form of a molecular dispersion.

5. The formulation of claim 1, wherein the content of the lipid component based on the binder component does not exceed 25% by weight.

6. The formulation of claim 1, wherein the binder is selected from polyvinylpyrolidones, vinylpyrrolidone copolymers with vinyl acetate, hydroxypropylcelluloses or hydroxypropylmethylcelluloses.

7. The formulation of claim 1, wherein the formulation is obtainable by melt extrusion of a plastic mixture comprising the components i), ii), and iii).

8. The formulation of claim 1, wherein at least part of the active pharmaceutical ingredient is in the form of a molecular dispersion, and wherein the binder is selected from polyvinylpyrrolidones, vinylpyrrolidone copolymers with vinyl acetate, hydroxypropylcelluloses or hydroxypropylmethylcelluloses.

9. The formulation of claim 1, wherein the formulation comprises 5 to 20% by weight of the active pharmaceutical ingredient.

10. The formulation of claim 9, wherein the formulation comprises 30 to 90% by weight of the binder component.

11. The formulation of claim 1, wherein the formulation is essentially amorphous.

12. The formulation of claim 11, wherein the lipid component has an HLB of not exceeding 8.

13. The formulation of claim 11, wherein the lipid component has an HLB of not exceeding 5.

14. The formulation of claim 11, wherein the binder component is a vinylpyrrolidone/vinyl acetate copolymer having a vinylpyrolidone: vinyl acetate ratio of 60:40.

15. The formulation of claim 11, wherein the formulation comprises 40 to 80% by weight of the binder component.

16. The formulation of claim 11, wherein the binder component is selected from polyvinylpyrrolidone, vinylpyrrolidone copolymer with vinyl acetate, hydroxypropylcellulose, hydroxypropylmethylcellulose, hydroxypropylmethylcellulose phthalate, or a mixture thereof.

17. The formulation of claim 16, wherein the formulation comprises 40 to 80% by weight of the binder component.

18. The formulation of claim 17, wherein the active pharmaceutical ingredient has a low solubility in water.

19. The formulation of claim 18, wherein the content of the lipid component based on the binder component does not exceed 25% by weight.

20. The formulation of claim 1, wherein the formulation is capable of spontaneously forming an emulsion upon contact with aqueous media which contains at least 50% by weight water.

21. The formulation of claim 1, wherein the lipid component is of liquid at room temperature.

22. The formulation of claim 1, wherein the lipid component has an HLB of not exceeding 5.

23. The formulation of claim 20, wherein the formulation is a tablet and comprises from 40 to 80% by weight of the binder component, and the content of the lipid component based on the binder component does not exceed 25% by weight.

24. The formulation of claim 11, wherein the formulation is a tablet and comprises from 40 to 80% by weight of the binder component, and the content of the lipid component based on the binder component does not exceed 25% by weight.

25. The formulation of claim 24, wherein the formulation is capable of spontaneously forming an emulsion upon contact with aqueous media contains at least 50% by weight water, and wherein the active pharmaceutical ingredient has low solubility in water.

26. The formulation of claim 25, wherein the lipid component is of liquid at room temperature.

27. The formulation of claim 25, wherein the lipid component has an HLB of not exceeding 5.

28. The formulation of claim 25, wherein the binder component is polyvinylpyrrolidone, vinylpyrrolidone coploymer with vinyl acetate, hydroxypropylcellulose, hydroypropylmethylcellulose, hydroypropylmethylcellulose phthalate, or a mixture thereof.

29. The formulation of claim 25, wherein the binder component is a vinylpyrrolidone/vinyl acetate copolymer with vinylpyrrolidone:vinyl acetate ratio of 60:40.

\* \* \* \* \*